United States Patent
Gobbi et al.

(10) Patent No.: US 10,457,685 B2
(45) Date of Patent: *Oct. 29, 2019

(54) [1,2,3]TRIAZOLO[4,5-D]PYRIMIDINE DERIVATIVES WITH AFFINITY FOR THE TYPE-2 CANNABINOID RECEPTOR

(71) Applicant: Hoffmann-La Roche Inc., Little Falls, NJ (US)

(72) Inventors: Luca Gobbi, Buus (CH); Uwe Grether, Efringen-Kirchen (DE); Wolfgang Guba, Mülheim (DE); Julian Kretz, Berlin (DE); Rainer E. Martin, Basel (CH); Matthias Valentin Westphal, Zurich (CH); Adriaan Pieter Ijzerman, Leiden (NL)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/228,539

(22) Filed: Dec. 20, 2018

(65) Prior Publication Data

US 2019/0127384 A1    May 2, 2019

Related U.S. Application Data

(63) Continuation of application No. PCT/EP2017/064994, filed on Jun. 20, 2017.

(30) Foreign Application Priority Data

Jun. 23, 2016 (EP) .................. 16175924

(51) Int. Cl.
| | | |
|---|---|---|
| C07D 487/04 | (2006.01) | |
| A61P 7/04 | (2006.01) | |
| A61P 9/10 | (2006.01) | |
| A61P 25/28 | (2006.01) | |
| A61P 37/08 | (2006.01) | |
| A61P 3/10 | (2006.01) | |
| A61P 29/00 | (2006.01) | |

(52) U.S. Cl.
CPC ............ *C07D 487/04* (2013.01); *A61P 3/10* (2018.01); *A61P 7/04* (2018.01); *A61P 9/10* (2018.01); *A61P 25/28* (2018.01); *A61P 29/00* (2018.01); *A61P 37/08* (2018.01)

(58) Field of Classification Search
CPC .................. C07D 487/04; A61K 31/519
USPC ........................ 544/254; 514/261.1
See application file for complete search history.

(56) References Cited

U.S. PATENT DOCUMENTS

| | | | |
|---|---|---|---|
| 7,776,889 B2 | 8/2010 | Chackalamannil et al. | |
| 8,741,906 B2 | 6/2014 | Adam et al. | |
| 9,056,866 B2 | 6/2015 | Adam et al. | |
| 9,067,943 B2 | 6/2015 | Bissantz et al. | |
| 9,505,762 B2 | 11/2016 | Bendels et al. | |
| 9,512,132 B2 | 12/2016 | Grether et al. | |
| 9,580,435 B2 | 2/2017 | Grether et al. | |
| 9,593,123 B2 | 3/2017 | Grether et al. | |
| 9,694,012 B2 | 7/2017 | Grether et al. | |
| 10,183,946 B2 | 1/2019 | Grether et al. | |
| 2019/0127383 A1 | 5/2019 | Gobbi et al. | |
| 2019/0127385 A1 | 5/2019 | Gobbi et al. | |
| 2019/0127386 A1 | 5/2019 | Gobbi et al. | |

FOREIGN PATENT DOCUMENTS

| | | |
|---|---|---|
| FR | 2 887 550 A1 | 6/2005 |
| WO | 2011/045068 A2 | 4/2011 |
| WO | 2013/068306 A1 | 5/2013 |
| WO | 2013/076182 A1 | 5/2013 |
| WO | 2014/135507 A1 | 9/2014 |
| WO | 2014/177490 A1 | 11/2014 |
| WO | 2014/177527 A1 | 11/2014 |
| WO | 2015/032769 A1 | 3/2015 |
| WO | 2016/071375 A1 | 5/2016 |
| WO | 2017/220516 A1 | 12/2017 |
| WO | 2017/220544 A1 | 12/2017 |
| WO | 2018/015088 A1 | 1/2018 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Layzer, Degenerative Diseases of the Nervous System, Cecil Textbook of Medicine, 20th Edition, vol. 2, pp. 2050-2057 (1996).*

(Continued)

*Primary Examiner* — Deepak R Rao
(74) *Attorney, Agent, or Firm* — Zong-Qiang Bill Tian

(57) ABSTRACT

The invention relates to a compound of formula (I)

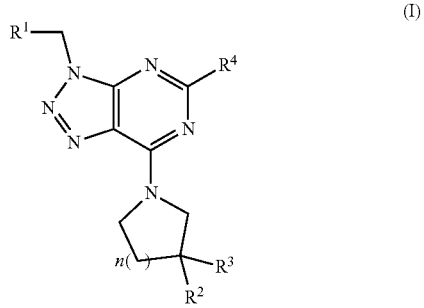

wherein $R^1$ to $R^4$ and n are defined as in the description and in the claims. The compound of formula (I) can be used as a medicament.

17 Claims, No Drawings

(56) References Cited

OTHER PUBLICATIONS

Damasio, Alzheimer's Disease and Related Dementias, Cecil Textbook of Medicine, 20th Edition, vol. 2, pp. 1992-1996 (1996).*
Starowicz et al., Cannabinoid receptors and pain, WIREs Membr Transp Signal 2:121-132 (2013).*
Adeniyi et al., "New drug design with covalent modifiers" Expert Opinion on Drug Discovery 11(1):79-90 (2016).
Akhmetshina et al., "The cannabinoid receptor CB2 exerts antifibrotic effects in experimental dermal fibrosis" Arthritis Rheumatism 60(4):1129-1136 (2009).
Ashton et al., "The cannabinoid CB2 receptor as a target for inflammation-dependent neurodegeneration" Current Neuropharmacology 5:73-80 (2007).
Bab et al., "Cannabinoid receptors and the regulation of bone mass" British Journal of Pharmacology 153:182-188 (2008).
Batkai et al., "Cannabinoid-2 receptor mediates protection against hepatic ischemia/reperfusion injury" The FASEB Journal 21:1788-1800 (2007).
Beltramo et al., "Cannabinoid type 2 receptor as a target for chronic-pain" Mini-Reviews in Medicinal Chemistry 9:11-25 (2009).
Cabral et al., "Cannabinoid receptors in microglia of the central nervous system: immune functional relevance" Journal of Leukocyte Biology 78:1192-1197 (2005).
Cabral et al., "CB $_2$ receptors in the brain: role in central immune function" British Journal of Pharmacology 153:240-251 (2008).
Centonze et al., "The endocannabinoid system in peripheral lymphocytes as a mirror of neuroinflammatory diseases" Current Pharmaceutical Design 14:2370-2383 (2008).
Defer et al., "The cannabinoid receptor type 2 promotes cardiac myocyte and fibroblast survival and protects against ischemia/reperfusion-induced cardiomyopathy" The FASEB Journal 23:2120-2130 (2009).
Fakhfouri et al., "WIN55212-2 attenuates amyloid-beta-induced neuroinflammation in rats through activation of cannabinoid receptors and PPAR-g pathway" Neuropharmacology 63:653-666 (2012).
Feizi et al., "The preventive effect of cannabinoids on reperfusion-induced ischemia of mouse kidney" Experimental and Toxicologic Pathology 60:405-410 (2008).
Garcia-Gonzalez et al., "Cannabinoids inhibit fibrogenesis in diffuse systemic sclerosis fibroblasts" Pheumatology 48:1050-1056 (2009).
García-Gutierrez et al., "Chronic blockade of cannabinoid CB2 receptors induces anxiolytic-like actions associated with alterations in GABA receptos" British Journal of Pharmacology 165:951-964 (2012).
International Preliminary Report on Patentability (IPRP) for PCT/EO2017/064994 dated Aug. 21, 2018.
International Search Report for PCT/EP2017/064994 dated Jul. 14, 2014.
Julien et al., "Antifibrogenic role of the cannabinoid receptor CB2 in the liver" Gastroenterology 128:742-755 (2005).
Lotersztajn et al., "CB2 receptors as new therapeutic targets for liver diseases" British Journal of Pharmacology 153:286-289 (2008).
Lotersztajn et al., "Le systeme cannabinoide: perspectives therapeutiques au cours des hepatopathies chroniques" Gastroenterol Clin Biol 31:255-258 (2007) (English Abstract).
Lunn et al., "A Novel Cannabinoid Peripheral Cannabinoid Recepto-Selective Inverse Agonist Blocks Leukocyte Recruitment in Vivo" Journal of Pharmacology and Experimental Therapeutics 316(2):780-788 (2006).
Mach et al., "The rold of the endocannabinoid system in atherosclerosis" Journal of Neuroendocrinology 20 (SUPPL 1):53-57 (2008).
Mallat et al., "Cannabinoid receptors as new targets of antifibrosing strategies during chronic liver diseases" Expert Opinion on Therapeutic Targets 11(3):403-409 (2007).
Miller et al., "CB $_2$ receptor-mediated migration of immunce cells: it can go either way" British Journal of Pharmacology 153:299-308 (2008).
Munoz-Luque et al., "Regression of fibrosis after chronic stimulation of cannabinoid CB2 receptor in cirrhotic rats" Journal of Pharmacology and Experimental Therapeutics 324(2):475-483 (2008).
Nettekoven et al., "Novel Triazolopyrimidine-Derived Cannabinoid Receptor 2 Agonists as Potential Treatment for Inflammatory Kidney Diseases" ChemMedChem 11(2):179-189 (2016).
Pacher et al., "Endocannabinoids and cannabinoid receptors in ischaemia-reperfusion injury and preconditioning" British Journal of Pharmacology 153:252-262 (2008).
Pacher et al., "Is lipid signaling through cannabinoid 2 receptors part of a protective system?" Progress in Lipid Research 50:193-211 (2011).
Pasquini et al., "Design, Synthesis, and Pharmacological Characterization of Indol-3-ylacetamides, Indol-3-yloxoacetamides, and Indol-3-ylcarboxmides: Potent and Selective CB2 Cannabinoid Receptor Inverse Agonists" Journal of Medicinal Chemistry 55:5391-5402 (2012).
Preet et al., "Cannabinoid Receptors, CB1 and CB2, as Novel Targets for Inhibition of Non-Small Cell Lung Cancer Growth and Metastasis" Cancer Prevention Research 4:65-75 (2011).
Qiao et al., "Synthesis and biological evaluation of indole-2-carboxamides bearing photoactivatable functionalities as novel allosteric modulators for the cannabinoid CB1 receptor" European Journal of Medicinal Chemistry 121:517-529 (2016).
Sophocleous et al., "Cannabinoid receptor antagonists inhibit osteoclast formation in vitro and ovariectomy-induced bone loss in vivo through CB1 and CB2 receptors" Calcified Tissue International Abstract OC18, 82:S31 (2008).
Ueda, "Involvement of cannabinoid CB2 receptors in the IgE-mediated triphasic cutaneous reaction in mice"Life Sciences 80:414-419 (2007).
Wright et al., "Cannabinoid CB $_2$ receptors in the gastrointestinal tract: a regulatory system in states of inflammation" British Journal of Pharmacology 153:263-270 (2008).
Yang et al., "Inhibition of hepatic tumor necrosis factor-αattenuates the anandamide-induced casoconstrictive response in cirrhotic rat livers" Liver International 29(5):678-685 (2009).
Zhang et al., "Cannabinoid CB $_2$ receptor activation decreses cerebal infarction in a mouse focal ischemia/reperfusion model" Journal of Cerebral Blood Flow & Metabolism 27:1387-1396 (2007).

* cited by examiner

[1,2,3]TRIAZOLO[4,5-D]PYRIMIDINE DERIVATIVES WITH AFFINITY FOR THE TYPE-2 CANNABINOID RECEPTOR

CROSS-REFERENCE TO RELATED APPLICATIONS

This application is a continuation of International Application No. PCT/EP2017/064994, filed on Jun. 20, 2017, which claims priority to European Patent Application No. 16175924.6, filed on Jun. 23, 2016, the contents of which are incorporated herein by reference in their entireties.

The present invention relates to novel [1,2,3]triazolo[4,5-d]pyrimidine derivatives with affinity for the type-2 cannabinoid (CB2) receptor, to the preparation thereof and to the diagnostic and therapeutic use thereof.

The invention relates in particular to a compound of formula (I)

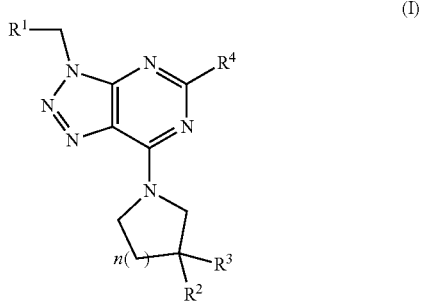

wherein
$R^1$ is a ring selected from phenyl and [1,2,5]oxadiazolyl wherein said ring is substituted with one substituent selected from halosulfonyl, halosulfonylalkyl, isothiocyanatoalkyl, isothiocyanato, aminoalkyldisulfanylalkyl, hydroxyalkyldisulfanylalkyl, hydroxyalkyldisulfanyl, aminoalkyldisulfanyl, halogen, alkyl, pyridinyldisulfanylalkyl, benzotriazolylsulfonylalkyl, dihydroxyalkyldisulfanylalkyl and pyridinyldisulfanyl and optionally further substituted with cyano;
$R^2$ and $R^3$ are independently selected from hydrogen, hydroxyl, halogen, thiohydroxyl, thiohydroxyazetidinyl, azido, isothiocyanato and alkyldisulfanyl;
provided that at least one of $R^1$, $R^2$ and $R^3$ is a group comprising sulfonyl, isothiocyanato, disulfanyl, thiohydroxyl or azido;
$R^4$ is alkyl or phenylhaloalkyl; and
n is 0 or 1;
or a pharmaceutically acceptable salt or ester thereof.

Novel [1,2,3]triazolo[4,5-d]pyrimidine derivatives that have high affinity and great selectivity towards the cannabinoid CB2 receptor have been found. These compounds have a modulatory effect on the activity of the CB2 receptor. The term 'modulatory effect' especially means agonist, antagonist and/or inverse agonist effects.

Agonists of the Cannabinoid Receptor 2 are useful for therapy and/or prophylaxis in a mammal. The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

Modulators of the Cannabinoid Receptor 2 are useful for therapy and/or prophylaxis in a mammal.

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemicpreconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the IR injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The interest in CB2 receptor ligands has been steadily on the rise during the last decade (currently 30-40 patent applications/year). Evidence from different sources support the view that lipid endocannabinoid signaling through CB2 receptors represents an aspect of the mammalian protective armamentarium (Pacher, P. Prog Lipid Res 2011, 50, 193). Its modulation by either selective CB2 receptor agonists or inverse agonists/antagonists (depending on the disease and its stage) holds unique therapeutic potential in a huge number of diseases. For CB2 inverse agonists/antagonists therapeutic opportunities have been demonstrated for many pathological conditions including pain (Pasquini, S. J Med Chem 2012, 55(11): 5391), neuropathic pain (Garcia-Gutierrez, M. S. Br J Pharmacol 2012, 165(4): 951), psychiatric disorders (Garcia-Gutierrez, M. S. Br J Pharmacol 2012, 165(4): 951), psychosis (Garcia-Gutierrez, M. S. Br J Pharmacol 2012, 165(4): 951), osteoporosis and inflammation (Sophocleous, A. Calcif Tissue Int 2008, 82(Suppl. 1):Abst OC18), psychiatric diseases and psychosis (Garcia-Gutierrez, M. S. Br J Pharmacol 2012, 165(4): 951), oncology (Preet, A. Cancer Prev Res 2011, 4: 65), encephalitis and malaria (Zimmer, A. WO 2011045068), allergy and inflammation (Ueda, Y. Life Sci 2007, 80(5): 414), encephalitis and malaria (Zimmer, WO 2011045068), asthma (Lunn, C. A. J Pharmacol Exp Ther 2006, 316(2): 780), immunological disorders (Fakhfouri, G. Neuropharmacology 2012, 63(4): 653), rheumatoid arthritis (Chackalamannil, S. U.S. Pat. No. 7,776,889), arthritis (Lunn, C. A. J Pharmacol Exp Ther 2006, 316(2): 780), and gastrointestinal disorders (Barth, F. FR 2887550).

The compounds of the invention bind to and modulate the CB2 receptor and have lower CB1 receptor activity.

The compounds of the invention contain functional groups such as sulfonyl fluoride, isothiocyanate, thiol, azide and methyldisulfanyl which can optionally be used to form a covalent bond with the CB2 receptor. Such small organic molecules as covalent modifiers can be used for the detection and localisation of the target, for imaging, and for therapeutic use (compare e.g. Adebayo A Adeniyi, Ramesh Muthusamy & Mahmoud E S Soliman, Expert Opin. Drug Discov. (2016) 11(1):79-90).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and tert.-butyl.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. A particular "haloalkyl" is difluoromethyl.

The terms "hydroxyl" and "hydroxy", alone or in combination, signify the —OH group.

The term "amino", alone or in combination, signifies the primary amino group (—$NH_2$), the secondary amino group (—NH—), or the tertiary amino group (—N—).

The term "sulfonyl", alone or in combination, means the —$SO_2$ group.

The term "disulfanyl", alone or in combination, means the —S—S— group.

The term "isothiocyanato", alone or in combination, means the —N═C═S group.

The terms "thiohydroxyl" or "thiohydroxy", alone or in combination, mean the —SH group.

The term "azido", alone or in combination, signifies the —N₃ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaoyloxymethyl esters. Additionally, any physiologically acceptable equivalents of the compounds of general formula (I), similar to the metabolically labile esters, which are capable of producing the parent compounds of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein $R^1$ is a ring selected from phenyl and [1,2,5]oxadiazolyl wherein said ring is substituted with one substituent selected from halosulfonyl, halosulfonylalkyl, isothiocyanatoalkyl, isothiocyanato, aminoalkyldisulfanylalkyl, hydroxyalkyldisulfanylalkyl, hydroxyalkyldisulfanyl, aminoalkyldisulfanyl, halogen and alkyl;

$R^2$ and $R^3$ are independently selected from hydrogen, hydroxyl, halogen, thiohydroxyl, thiohydroxyazetidinyl, azido, isothiocyanato and alkyldisulfanyl;

provided that at least one of $R^1$, $R^2$ and $R^3$ is a group comprising sulfonyl, isothiocyanato, disulfanyl, thiohydroxyl or azido;

$R^4$ is alkyl or phenylhaloalkyl; and n is 0 or 1;

or a pharmaceutically acceptable salt or ester thereof.

The invention further relates to:

A compound of formula (I) wherein $R^1$ is a ring selected from phenyl and [1,2,5]oxadiazolyl wherein said ring is substituted with one substituent selected from halosulfonyl, halosulfonylalkyl, isothiocyanatoalkyl, isothiocyanato, halogen and alkyl;

A compound of formula (I) wherein $R^1$ is a ring selected from phenyl and [1,2,5]oxadiazolyl wherein said ring is substituted with one substituent selected from fluorosulfonyl, fluorosulfonylmethyl, isothiocyanatomethyl, isothiocyanato, chloro and methyl;

A compound of formula (I) wherein $R^1$ is fluorosulfonylphenyl, fluorosulfonylmethylphenyl, isothiocyanatomethylphenyl, isothiocyanatophenyl, chlorophenyl and mehtyl[1,2,5]oxadiazolyl;

A compound of formula (I) wherein $R^2$ is hydrogen and $R^3$ is hydroxyl, thiohydroxyl, azido, isothiocyanato or methyldisulfanyl, or $R^2$ and $R^3$ are both fluoro at the same time;

A compound of formula (I) wherein $R^4$ is tert.-butyl or phenyldifluoromethyl; and A compound of formula (I) wherein n is 1;

A compound of formula (I) wherein $R^1$ is a ring selected from phenyl and [1,2,5]oxadiazolyl wherein said ring is substituted with one substituent selected from halosulfonyl, halosulfonylalkyl, isothiocyanatoalkyl, isothiocyanato, halogen, alkyl, hydroxyalkyldisulfanylalkyl, pyridinyldisulfanylalkyl, dihydroxyalkyldisulfanylalkyl and optionally further substituted with cyano.

A compound of formula (I) wherein $R^1$ is a ring selected from phenyl and [1,2,5]oxadiazolyl wherein said ring is substituted with one substituent selected from fluorosulfonyl, fluorosulfonylmethyl, isothiocyanatomethyl, isothiocyanato, chloro, methyl, hydroxyethyldisulfanylethyl, fluorosulfonylethyl, pyridinyldisulfanylethyl, dihydroxyethyldisulfanylethyl and optionally further substituted with cyano; and A compound of formula (I) wherein $R^1$ is fluorosulfonylphenyl, fluorosulfonylmethylphenyl, isothiocyanatomethylphenyl, isothiocyanatophenyl, chlorophenyl, mehtyl[1,2,5]oxadiazolyl, hydroxyethyldisulfanylethylphenyl, fluorosulfonylethylphenyl, pyridinyldisulfanylethylphenyl, dihydroxyethyldisulfanylethylphenyl or (fluorosulfonyl)(cyano)phenyl.

The invention further relates to a compound of formula (I) selected from:

2-({5-tert-butyl-7-[(3S)-3-hydroxypyrrolidin-1-yl]-3H-[1,2,3]triazolo[4,5-d]pyrimidin-3-yl}methyl)benzene-1-sulfonyl fluoride;

(2-{[5-tert-butyl-7-(3,3-difluoropyrrolidin-1-yl)-3H-[1,2,3]triazolo[4,5-d]pyrimidin-3-yl]methyl}phenyl)methanesulfonyl fluoride;

[2-({5-tert-butyl-7-[(3S)-3-hydroxypyrrolidin-1-yl]-3H-[1,2,3]triazolo[4,5-d]pyrimidin-3-yl}methyl)phenyl]methanesulfonyl fluoride;

5-tert-butyl-7-(3,3-difluoropyrrolidin-1-yl)-3-{[2-(isothiocyanatomethyl)phenyl]methyl}-3H-[1,2,3]triazolo[4,5-d]pyrimidine;

(3S)-1-(5-tert-butyl-3-{[2-(isothiocyanatomethyl)phenyl]methyl}-3H-[1,2,3]triazolo[4,5-d]pyrimidin-7-yl)pyrrolidin-3-ol;

5-tert-butyl-7-(3,3-difluoropyrrolidin-1-yl)-3-[(2-isothiocyanatophenyl)methyl]-3H-[1,2,3]triazolo[4,5-d]pyrimidine;

2-{[5-tert-butyl-7-(3,3-difluoropyrrolidin-1-yl)-3H-[1,2,3]triazolo[4,5-d]pyrimidin-3-yl]methyl}benzene-1-sulfonyl fluoride;

2-{[(2-{[5-tert-butyl-7-(3,3-difluoropyrrolidin-1-yl)-3H-[1,2,3]triazolo[4,5-d]pyrimidin-3-yl]methyl}phenyl)methyl]disulfanyl}ethan-1-amine;

2-{[(2-{[5-tert-butyl-7-(3,3-difluoropyrrolidin-1-yl)-3H-[1,2,3]triazolo[4,5-d]pyrimidin-3-yl]methyl}phenyl)methyl]disulfanyl}ethan-1-ol;

2-[(2-{[5-tert-butyl-7-(3,3-difluoropyrrolidin-1-yl)-3H-[1,2,3]triazolo[4,5-d]pyrimidin-3-yl]methyl}phenyl)disulfanyl]ethan-1-ol;

2-[(2-{[5-tert-butyl-7-(3,3-difluoropyrrolidin-1-yl)-3H-[1,2,3]triazolo[4,5-d]pyrimidin-3-yl]methyl}phenyl)disulfanyl]ethan-1-amine;

2-{[2-({5-[difluoro(phenyl)methyl]-7-(3,3-difluoropyrrolidin-1-yl)-3H-[1,2,3]triazolo[4,5-d]pyrimidin-3-yl}methyl)phenyl]disulfanyl}ethan-1-amine;

2-({[2-({5-[difluoro(phenyl)methyl]-7-(3,3-difluoropyrrolidin-1-yl)-3H-[1,2,3]triazolo[4,5-d]pyrimidin-3-yl}methyl)phenyl]methyl}disulfanyl)ethan-1-amine;

2-({5-[difluoro(phenyl)methyl]-7-[(3S)-3-hydroxypyrrolidin-1-yl]-3H-[1,2,3]triazolo[4,5-d]pyrimidin-3-yl}methyl)benzene-1-sulfonyl fluoride;

2-({5-[difluoro(phenyl)methyl]-7-(3,3-difluoropyrrolidin-1-yl)-3H-[1,2,3]triazolo[4,5-d]pyrimidin-3-yl}methyl)benzene-1-sulfonyl fluoride;

[2-({5-[difluoro(phenyl)methyl]-7-[(3S)-3-hydroxypyrrolidin-1-yl]-3H-[1,2,3]triazolo[4,5-d]pyrimidin-3-yl}methyl)phenyl]methanesulfonyl fluoride;

[2-({5-[difluoro(phenyl)methyl]-7-(3,3-difluoropyrrolidin-1-yl)-3H-[1,2,3]triazolo[4,5-d]pyrimidin-3-yl}methyl)phenyl]methanesulfonyl fluoride;

(3S)-1-(5-[difluoro(phenyl)methyl]-3-{[2-(isothiocyanatomethyl)phenyl]methyl}-3H-[1,2,3]triazolo[4,5-d]pyrimidin-7-yl)pyrrolidin-3-ol;

5-[difluoro(phenyl)methyl]-7-(3,3-difluoropyrrolidin-1-yl)-3-{[2-(isothiocyanatomethyl)phenyl]methyl}-3H-[1,2,3]triazolo[4,5-d]pyrimidine;

5-[difluoro(phenyl)methyl]-7-(3,3-difluoropyrrolidin-1-yl)-3-[(2-isothiocyanatophenyl)methyl]-3H-[1,2,3]triazolo[4,5-d]pyrimidine;

1-{5-tert-butyl-3-[(2-chlorophenyl)methyl]-3H-[1,2,3]triazolo[4,5-d]pyrimidin-7-yl}pyrrolidine-3-thiol;

1-{5-tert-butyl-3-[(2-chlorophenyl)methyl]-3H-[1,2,3]triazolo[4,5-d]pyrimidin-7-yl}azetidine-3-thiol;

(3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

(3R)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

(3S)-1-{5-tert-butyl-3-[(2-chlorophenyl)methyl]-3H-[1,2,3]triazolo[4,5-d]pyrimidin-7-yl}pyrrolidine-3-thiol;

(3R)-1-{5-tert-butyl-3-[(2-chlorophenyl)methyl]-3H-[1,2,3]triazolo[4,5-d]pyrimidin-7-yl}pyrrolidine-3-thiol 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine;

5-tert-butyl-3-[(2-chlorophenyl)methyl]-7-(3-isothiocyanatopyrrolidin-1-yl)-3H-[1,2,3]triazolo[4,5-d]pyrimidine;

5-tert-butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine;

7-(3-azidopyrrolidin-1-yl)-5-tert-butyl-3-[(2-chlorophenyl)methyl]-3H-[1,2,3]triazolo[4,5-d]pyrimidine;

5-[difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine;

3-[(2-chlorophenyl)methyl]-5-[difluoro(phenyl)methyl]-7-[3-(methyldisulfanyl)pyrrolidin-1-yl]-3H-[1,2,3]triazolo[4,5-d]pyrimidine;

7-(3-azidopyrrolidin-1-yl)-5-[difluoro(phenyl)methyl]-3-[(4-methyl-1,2,5-oxadiazol-3-yl)methyl]-3H-[1,2,3]triazolo[4,5-d]pyrimidine;

7-(3-azidopyrrolidin-1-yl)-3-[(2-chlorophenyl)methyl]-5-[difluoro(phenyl)methyl]-3H-[1,2,3]triazolo[4,5-d]pyrimidine;

3-[(2-chlorophenyl)methyl]-5-[difluoro(phenyl)methyl]-7-(3-isothiocyanatopyrrolidin-1-yl)-3H-[1,2,3]triazolo[4,5-d]pyrimidine;

5-[difluoro(phenyl)methyl]-7-(3-isothiocyanatopyrrolidin-1-yl)-3-[(4-methyl-1,2,5-oxadiazol-3-yl)methyl]-3H-[1,2,3]triazolo[4,5-d]pyrimidine;

2-[[5-[difluoro(phenyl)methyl]-7-[(3S)-3-hydroxypyrrolidin-1-yl]triazolo[4,5-d]pyrimidin-3-yl]methyl]benzenesulfonyl fluoride;

2-[[2-[[5-tert-butyl-7-(3,3-difluoropyrrolidin-1-yl)triazolo[4,5-d]pyrimidin-3-yl]methyl]phenyl]methyldisulfanyl]ethanol;

2-[[5-[difluoro(phenyl)methyl]-7-(3,3-difluoropyrrolidin-1-yl)triazolo[4,5-d]pyrimidin-3-yl]methyl]benzenesulfonyl fluoride;

5-[difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine;

2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanol;

2-[2-[2-[[5-tert-butyl-7-(3,3-difluoropyrrolidin-1-yl)triazolo[4,5-d]pyrimidin-3-yl]methyl]phenyl]ethyldisulfanyl]ethanol;

3-[[2-[2-(benzotriazol-1-ylsulfonyl)ethyl]phenyl]methyl]-5-tert-butyl-7-(3,3-difluoropyrrolidin-1-yl)triazolo[4,5-d]pyrimidine;

2-[2-[[5-tert-butyl-7-(3,3-difluoropyrrolidin-1-yl)triazolo[4,5-d]pyrimidin-3-yl]methyl]phenyl]ethanesulfonyl fluoride;

5-tert-butyl-7-(3,3-difluoropyrrolidin-1-yl)-3-[[2-[2-(pyridin-2-yldisulfanyl)ethyl]phenyl]methyl]triazolo[4,5-d]pyrimidine;

2-[2-[2-[[5-tert-butyl-7-(3,3-difluoropyrrolidin-1-yl)triazolo[4,5-d]pyrimidin-3-yl]methyl]phenyl]ethyldisulfanyl]ethanamine;

2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanamine;

3-[2-[2-[[5-tert-butyl-7-(3,3-difluoropyrrolidin-1-yl)triazolo[4,5-d]pyrimidin-3-yl]methyl]phenyl]ethyldisulfanyl]propane-1,2-diol;

2-[[2-[[5-tert-butyl-7-(3,3-difluoropyrrolidin-1-yl)triazolo[4,5-d]pyrimidin-3-yl]methyl]phenyl]disulfanyl]ethanol;

5-tert-butyl-7-(3,3-difluoropyrrolidin-1-yl)-3-[[2-(pyridin-2-yldisulfanyl)phenyl]methyl]triazolo[4,5-d]pyrimidine; and 2-[[5-tert-butyl-7-(3,3-difluoropyrrolidin-1-yl)triazolo[4,5-d]pyrimidin-3-yl]methyl]-3-ethynylbenzenesulfonyl fluoride.

The invention also relates to a compound of formula (I) selected from:

2-({5-tert-butyl-7-[(3S)-3-hydroxypyrrolidin-1-yl]-3H-[1,2,3]triazolo[4,5-d]pyrimidin-3-yl}methyl)benzene-1-sulfonyl fluoride;

(2-{[5-tert-butyl-7-(3,3-difluoropyrrolidin-1-yl)-3H-[1,2,3]triazolo[4,5-d]pyrimidin-3-yl]methyl}phenyl)methanesulfonyl fluoride;

5-tert-butyl-7-(3,3-difluoropyrrolidin-1-yl)-3-{[2-(isothiocyanatomethyl)phenyl]methyl}-3H-[1,2,3]triazolo[4,5-d]pyrimidine;

(3S)-1-(5-tert-butyl-3-{[2-(isothiocyanatomethyl)phenyl]methyl}-3H-[1,2,3]triazolo[4,5-d]pyrimidin-7-yl)pyrrolidin-3-ol;

5-tert-butyl-7-(3,3-difluoropyrrolidin-1-yl)-3-[(2-isothiocyanatophenyl)methyl]-3H-[1,2,3]triazolo[4,5-d]pyrimidine;

2-{[5-tert-butyl-7-(3,3-difluoropyrrolidin-1-yl)-3H-[1,2,3]triazolo[4,5-d]pyrimidin-3-yl]methyl}benzene-1-sulfonyl fluoride;

1-{5-tert-butyl-3-[(2-chlorophenyl)methyl]-3H-[1,2,3]triazolo[4,5-d]pyrimidin-7-yl}pyrrolidine-3-thiol;

(3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine;

5-tert-butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine;

5-[difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine;

7-(3-azidopyrrolidin-1-yl)-3-[(2-chlorophenyl)methyl]-5-[difluoro(phenyl)methyl]-3H-[1,2,3]triazolo[4,5-d]pyrimidine;

2-[[5-[difluoro(phenyl)methyl]-7-(3,3-difluoropyrrolidin-1-yl)triazolo[4,5-d]pyrimidin-3-yl]methyl]benzenesulfonyl fluoride;

2-[2-[2-[[5-tert-butyl-7-(3,3-difluoropyrrolidin-1-yl)triazolo[4,5-d]pyrimidin-3-yl]methyl]phenyl]ethyldisulfanyl]ethanol;

2-[2-[[5-tert-butyl-7-(3,3-difluoropyrrolidin-1-yl)triazolo[4,5-d]pyrimidin-3-yl]methyl]phenyl]ethanesulfonyl fluoride;

5-tert-butyl-7-(3,3-difluoropyrrolidin-1-yl)-3-[[2-[2-(pyridin-2-yldisulfanyl)ethyl]phenyl]methyl]triazolo[4,5-d]pyrimidine;

3-[2-[2-[[5-tert-butyl-7-(3,3-difluoropyrrolidin-1-yl)triazolo[4,5-d]pyrimidin-3-yl]methyl]phenyl]ethyldisulfanyl]propane-1,2-diol; and 2-[[5-tert-butyl-7-(3,3-difluoropyrrolidin-1-yl)triazolo[4,5-d]pyrimidin-3-yl]methyl]-3-ethynylbenzenesulfonyl fluoride.

The preparation of compounds of formula (I) of the present invention may be carried out in sequential or convergent synthetic routes. Syntheses of the compounds of the invention are shown in the following scheme. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). We found it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

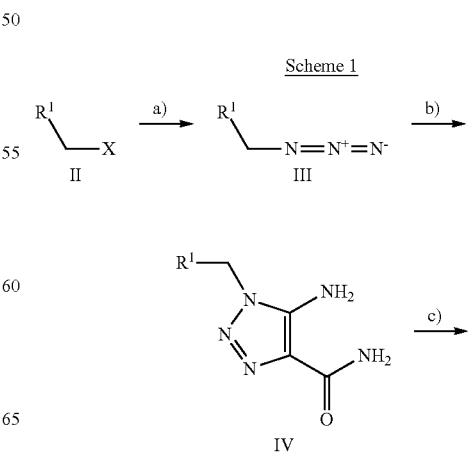

Scheme 1

-continued

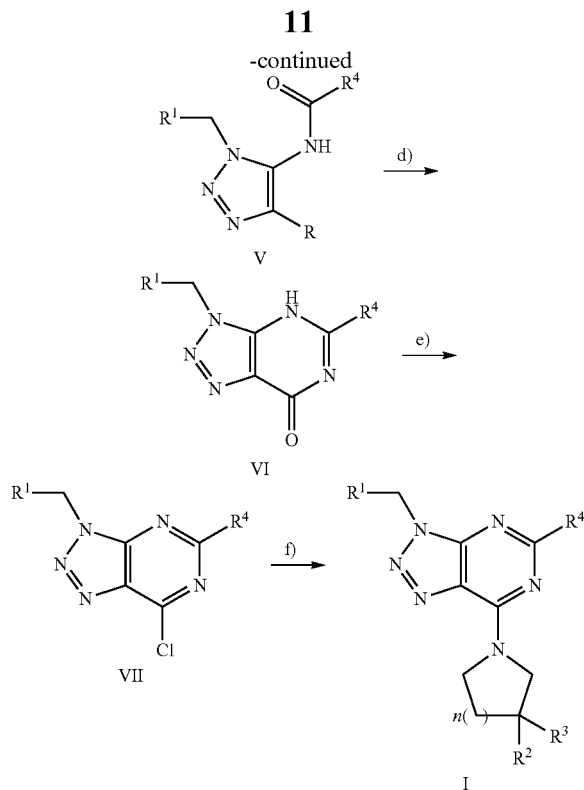

X = Br or Cl
R = CONH$_2$, CN a) Halides II are either commercially available or can be synthesized according to methods known in the art. These halides II are conveniently reacted with sodium azide in a suitable solvent such as acetonitrile, ethanol or DMF to afford azide derivatives III. Alternative preferred conditions involve the use of solvents like DMA, NMP or DMSO, even more preferred are NMP and DMSO. In polar aprotic solvents like NMP and DMSO, the alkylations can usually be conducted at lower temperature than for example in acetonitrile, often at room temperature to 40° C. (this is the case for example for BnCl, 1-chloro-2-(chloromethyl)benzene or PMB-Cl; this depends of course on the reactivity of the halides II) and hence provide a better process safety window (caution organic azides are of course known to be potentially dangerous and process safety has always to be carefully assessed). The addition of water can be beneficial as it increases the solubility of sodium azide and provided more robust kinetic profiles as it helps to dissolves hard clumps of NaN$_3$. It can also lead to a better filterability of the final azide reaction mixture. Filtration of the reaction mixture might be required for example when the following cycloaddition is performed in a continuous mode in small channels reactors. The azide is not isolated and its solution is best introduced in the next step. This also avoids its isolation which can also lead to safety issues.

b) Triazole derivatives IV can be prepared by a [3+2] cycloaddition of azide derivatives III with 2-cyanoacetamide in the presence of an appropriate base such as sodium methoxide or sodium ethoxide in a suitable solvent such as methanol, ethanol or DMF. Alternative preferred conditions involve reacting the azide with 2-cyanoacetamide in solvents like NMP or DMSO, in the presence of sodium hydroxide. The batch process is usually performed at room temperature to 50° C., preferably between room temperature and 40° C. (caution, process safety has always to be carefully assessed). The cycloaddition process is also amendable to continuous mode (for a relevant literature example, see Org. Process Res. Dev., 2009, 13 (6), pp 1401-1406) and in this case the reaction temperature can be increased above 50° C., for example (but not limited to) between 50° C. and 90° C., preferably between 60° C. and 70° C.

c) Triazole derivatives V can be obtained by acylation of IV with an acyl-halide in the presence of a base such as DIEA, DMAP, pyridine and the like. Double acylation and the formation of nitrile side products have been observed. These can be significant when working for example in pyridine as solvent. However, these can be minimized when using DMA or NMP, preferably DMA as solvent instead of pyridine. Preferred conditions involves the use of 1.0-2 equiv. of pyridine and pivaloyl chloride, preferably 1.0 to 1.5 equiv., preferably around 1.5 equiv at 50-100° C., preferably between 75-85° C. These high boiling polar solvents also allow telescoping the following cyclization step which greatly simplifies the process.

d) Triazolopyrimidine derivatives VI can be prepared by intramolecular cyclization oftriazole derivative V in the presence of a base such as KHCO$_3$, Na$_2$CO$_3$ and water either with or without a solvent such as methanol, ethanol, dioxane and toluene. Alternative preferred conditions involve the use of DMA or NMP as solvents, preferably DMA. The reaction can be performed in the presence of KHCO$_3$ at 130-170° C., preferably between 140 and 160° C. Compound VI may exist as a tautomer or a mixture of tautomers, for example:

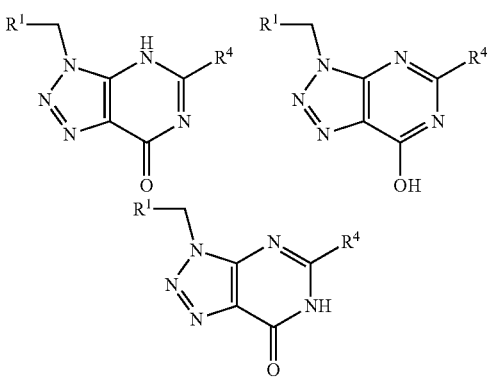

Optionally amido amides IV can be reacted with nitriles R$^4$—CN in the presence of a base such as K$_2$CO$_3$ in a solvent such as DMF, preferentially at temperatures close to the boiling point of the solvent to directly arrive at pyrimidones VI.

e) Chlorides VII can be obtained by reaction of VI with a chlorination reagent such as POCl$_3$, SOCl$_2$ or (COCl)$_2$ in the presence of an appropriate base such as N,N-diethyl aniline, lutidine, or pyridine. Alternative preferred conditions involve the use of the Vilsmeier reagent as chlorinating agent. It can also be generated in situ by reacting oxalyl chloride with DMF. The chlorination can be performed for example in acetonitrile, DCM or AcOEt, preferably in DCM. These conditions allow for mild reaction temperature and for example, avoid the quench of excess POCl$_3$ upon work-up. The crude product can be introduced in the next step.

f) Chlorides VII are conveniently reacted with amine nucleophiles in the presence of an appropriate base such as triethylamine, DIEA or DBU in a suitable solvent such as acetonitrile, methanol, toluene or DMF to yield triazolopyrimidine derivatives I.

These derivatives can be the final compounds, however preferably when $R^1$—$CH_2$=substituted benzyl group such as p-methoxy benzyl, these groups can be cleaved with TFA, CAN, hydrogenation and the like to access derivatives I ($R^1$—$CH_2$=H). $R^1$—$CH_2$=benzyl represents a suitable alternative protecting group. It avoids the use of PMB-Cl (for the preparation of the corresponding azide intermediate III) which is known to have some thermal stability issues (see for example *Organic Process Research & Development* 2005, 9, 1009-1012) and varying quality depending on the supplier. The benzyl group can be cleaved under standard hydrogenolysis conditions also for example in the presence of acids. When HCl is used, the derivatives I ($R^1$—$CH_2$=H) can potentially be isolated as salts.

The triazole derivatives I ($R^1$—$CH_2$=H) is conveniently reacted either with a halide (or sulfonate such as a mesylate, a nonaflate or a tosylate) in the presence of suitable base such as DIEA, DBU, $K_2CO_3$, or $Cs_2CO_3$ in a solvent such as DMF, dioxane or toluene, or alternatively with an alcohol under Mitsunobu reaction conditions using suitable diazodicarboxylate (DEAD, DIAD and the like) and phosphine such as $PBu_3$ or $PPh_3$ in an appropriate solvent such as THF, DCM, toluene to afford final triazolo-pyrimidine derivatives I.

If one of the starting materials, compounds of formulae II, acylation reagents used in step c) or amines used in step f), contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3ʳ edition) can be introduced before the critical step applying methods well known in the art. Such protecting groups can be removed at a later stage of the synthesis using standard methods known in the art.

If one or more compounds of formulae II to VII, acylation reagents used in step d) or amines used in step f), contain chiral centers, triazolopyrimidines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising the reaction of a compound of formula (A)

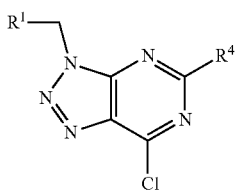

(A)

in the presence of a compound of formula (B)

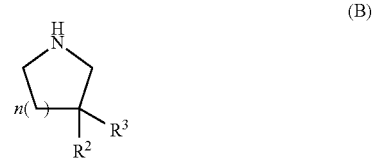

(B)

and a base, wherein $R^1$ to $R^4$ and n are as defined above.

In the process of the invention, the base is for example triethylamine, DIEA or DBU.

In the process of the invention, a solvent can be used, which can be selected for example from acetonitrile, methanol, toluene and DMF.

The invention thus also relates to a compound of formula (I) when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8.

In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration.

Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention thus also relates to:

A compound of formula (I) for use as therapeutically active substance;

A pharmaceutical composition comprising a compound of formula (I) and a therapeutically inert carrier;

The use of a compound of formula (I) for the preparation of medicaments for the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy;

A compound of formula (I) for use in the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy;

A method for the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy, which method comprises administering an effective amount of a compound of formula (I) to a patient in need thereof; and The use of a compound of formula (I) for the detection or the imaging of the CB2 receptor.

The invention will now be illustrated by the following examples which have no limiting character.

EXAMPLES

Abbreviations

MS=mass spectrometry; CAN=ceric ammonium nitrate; CAN=chemical abstract service number; Ac=acetyl; DIEA=N,N-diisopropylethylamine; DBU=1,8-Diazabicyclo [5.4.0]undec-7-ene; DMF=dimethylformamide; HPLC=LC=high performance liquid chromatography; HRMS=high resolution mass spectrometry; MeCN=acetonitrile; NBS=N-Bromosuccinimide; NCS=N-Chloroosuccinimide; NMR data are reported in parts per million (6) relative to internal tetramethylsilane and are referenced to the deuterium lock signal from the sample solvent ($d_6$-DMSO unless otherwise stated); coupling constants (J) are in Hertz; THF= tetrahydrofurane; TFA=trifluoroacetic acid; DCM=dichloro- methane.

Example 1

2-[[5-tert-Butyl-7-[(3S)-3-hydroxypyrrolidin-1-yl] triazolo[4,5-d]pyrimidin-3-yl]methyl]benzenesulfonyl fluoride

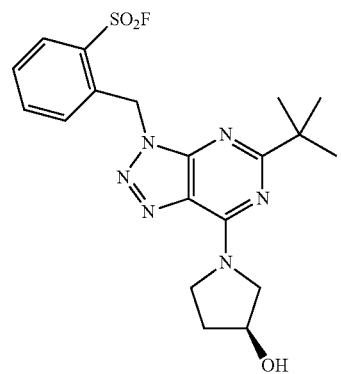 [SMILES: CC(C)(C)c1nc(N2CC[C@H](O)C2)c2nnn(Cc3ccccc3S(=O)(=O)F)c2n1]

a) 2-(Bromomethyl)benzene-1-sulfonyl fluoride

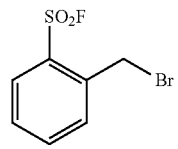 [SMILES: O=S(=O)(F)c1ccccc1CBr]

A mixture of phenylmethylsulfonyl fluoride (CAS 444-31-5, 350 mg, 2.01 mmol, 1 equiv), NBS (429 mg, 2.41 mmol, 1.2 equiv) and AIBN (33 mg, 0.20 mmol, 0.1 equiv)

in MeCN (2.00 mL) was refluxed overnight. The solvent was removed and toluene (5 mL) was added. The suspension was filtered over celite (rinsing with additional toluene) and the filtrate was concentrated. Flash chromatography on silica (1.5% EtOAc in hexanes) afforded 2-(bromomethyl)benzene-1-sulfonyl fluoride (407 mg, 1.6 mmol, 80% yield) as a colorless solid. HRMS (EI+) 251.9251 (M$^+$).

b) 2-[[5-tert-Butyl-7-[(3S)-3-hydroxypyrrolidin-1-yl]triazolo[4,5-d]pyrimidin-3-yl]methyl]benzenesulfonyl fluoride (3S)-1-(5-tert-Butyl-3H-triazolo[4,5-d]pyrimidin-7-yl)pyrrolidin-3-ol (CAS 1433946-74-7, 50 mg, 0.19 mmol, 1.0 equiv) and 2-(bromomethyl)benzene-1-sulfonyl fluoride (53 mg, 0.21 mmol, 1.1 equiv) were dissolved in DMF (1.0 mL) at room temperature. Then NEt$_3$ (40 µl, 0.29 mmol, 1.5 equiv) was added and the reaction mixture was stirred for 1 h. The mixture was diluted with EtOAc (20 mL), washed with 5% aq. LiCl (2×2 mL) and brine (1×5 mL), dried over MgSO$_4$, filtered and concentrated. Flash chromatography on silica (EtOAc/hexanes/AcOH 5:5:1) afforded 2-[[5-tert-butyl-7-[(3S)-3-hydroxypyrrolidin-1-yl]triazolo[4,5-d]pyrimidin-3-yl]methyl]benzenesulfonyl fluoride (23 mg, 0.053 mmol, 28% yield) as colorless oil. HRMS (ESI+) 435.1607 (M+H$^+$).

Example 2

(2-{[5-tert-Butyl-7-(3,3-difluoropyrrolidin-1-yl)-3H-[1,2,3]triazolo[4,5-d]pyrimidin-3-yl]methyl}phenyl)methanesulfonyl fluoride

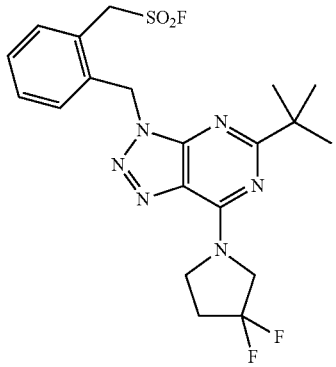 [SMILES: CC(C)(C)c1nc(N2CCC(F)(F)C2)c2nnn(Cc3ccccc3CS(=O)(=O)F)c2n1]

a) o-Tolylmethanesulfonyl fluoride

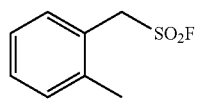

1-(Chloromethyl)-2-methylbenzene (CAS 552-45-4, 3.35 g, 23.8 mmol, 1.00 equiv) and thiourea (1.81 g, 23.8 mmol, 1.00 equiv) were combined with EtOH (24 mL) and refluxed for 1 h. The solvent was removed to leave a colorless solid. MeCN (34.3 mL) and aq. HCl (2 M, 6.9 mL) were added and it was stirred until most of the solid was dissolved. NCS (12.7 g, 95.1 mmol, 4 equiv) was then added in portions at such a rate that the temperature did not rise above 23° C. (internal temperature, cooling with icebath). After completion of the addition, the cooling bath was removed and the yellow mix was stirred for 30 minutes.

It was then poured into an addition funnel containing water (100 mL), the transfer was quantitated with the help of ether. The aq. phase was then extracted with diethylether (3×50 mL). The combined organics were washed with sat. aq. NaHCO$_3$ (30 mL) and brine (30 mL), dried over MgSO$_4$, filtered and concentrated to give 5.84 g of crude material, which was dissolved in a 3:1 mix of acetone:water (100 mL). Potassium fluoride was added (2.77 g, 47.6 mmol, 2 equiv). After stirring overnight, the mix was diluted with water (300 mL) and extracted with ether (3×100 mL). The combined organics were washed with sat. aq. NaHCO$_3$ (30 mL), water (30 mL) and brine (30 mL), dried over MgSO$_4$, filtered and concentrated. Flash chromatography on silica (5% EtOAc in hexanes) afforded o-tolylmethanesulfonyl fluoride (2.04 g, 10.8 mmol, 45.5% yield) as colorless oil that solidified overnight. HRMS (EI+) 188.0303 (M$^+$).

b) (2-(Bromomethyl)phenyl)methanesulfonyl fluoride

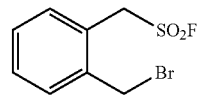 [SMILES: O=S(=O)(F)Cc1ccccc1CBr]

o-Tolylmethanesulfonyl fluoride (188 mg, 1.00 mmol, 1 equiv), NBS (196 mg, 1.10 mmol, 1.1 equiv) and benzoyl peroxide (32.3 mg, 0.10 mmol, 0.1 equiv) were combined with CCl$_4$ (5.00 mL) and refluxed for 3 h. Solvent removal and flash chromatography on silica (15% CH$_2$Cl$_2$ in hexanes) afforded (2-(bromomethyl)phenyl)methanesulfonyl fluoride as colorless solid (213 mg, 0.750 mmol, purity 94% (6% starting material), 71% yield). HRMS (EI+) 265.9410 (M$^+$).

c) (2-{[5-tert-Butyl-7-(3,3-difluoropyrrolidin-1-yl)-3H-[1,2,3]triazolo[4,5-d]pyrimidin-3-yl]methyl}phenyl)methanesulfonyl fluoride In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from 5-tert-butyl-7-(3,3-difluoropyrrolidin-1-yl)-3H-[1,2,3]triazolo[4,5-d]pyrimidine (CAS 1438465-59-8, 50 mg, 0.18 mmol) and (2-(bromomethyl)phenyl)methanesulfonyl fluoride and isolated as colorless oil (15 mg, 0.032 mmol, 18% yield). HRMS (ESI+) 469.1624 (M+H$^+$).

Example 3

[2-({5-tert-Butyl-7-[(3S)-3-hydroxypyrrolidin-1-yl]-3H-[1,2,3]1 triazolo[4,5-d]pyrimidin-3-yl}methyl)phenyl]methanesulfonyl fluoride

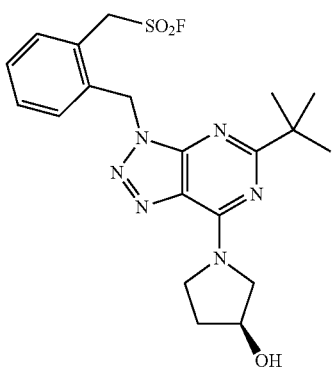 [SMILES: CC(C)(C)c1nc(N2CC[C@H](O)C2)c2nnn(Cc3ccccc3CS(=O)(=O)F)c2n1]

In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from (3S)-1-(5-tert-butyl-3H-triazolo[4,5-d]pyrimidin-7-yl)pyrrolidin-3-ol (CAS 1433946-74-7, 55 mg, 0.21 mmol, 1.0 equiv) and (2-(bromomethyl)phenyl)methanesulfonyl fluoride and isolated as colorless oil (31 mg, 0.069 mmol, 33% yield). HRMS (ESI+) 449.1767 (M+H$^+$).

Example 4

5-tert-Butyl-7-(3,3-difluoropyrrolidin-1-yl)-3-{[2-(isothiocyanatomethyl)phenyl]methyl}-3H-[1,2,3]triazolo[4,5-d]pyrimidine

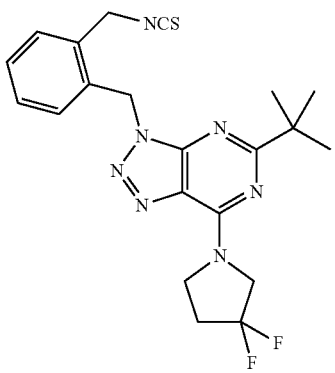

a) 1-(Azidomethyl)-2-(chloromethyl)benzene

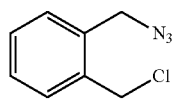

o-Xylylene dichloride (CAS 612-12-4, 3.23 g, 18.4 mmol, 1.00 equiv) was dissolved in DMSO (18.4 mL) and NaN$_3$ (1.20 g, 18.4 mmol, 1.00 equiv) was added. After 2 h, the reaction mix was diluted with water (200 mL) and extracted with EtOAc (3×70 mL). The organic phase was washed with brine (2×20 mL), dried over MgSO$_4$, filtered and concentrated. Repeated flash chromatography on silica (2% EtOAc in hexanes) afforded 1-(azidomethyl)-2-(chloromethyl)benzene (520 mg, 2.86 mmol, 15.5% yield) as colorless oil. $^1$H NMR (400 MHz, CDCl$_3$) δ=7.48-7.32 (m, 4H), 4.68 (s, 2H), 4.53 (s, 2H). $^{13}$C NMR (101 MHz, CDCl$_3$) δ=136.0, 134.3, 130.8, 130.2, 129.4, 129.2, 52.1, 43.6.

b) 1-(Chloromethyl)-2-(isothiocyanatomethyl)benzene

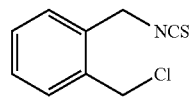

1-(Azidomethyl)-2-(chloromethyl)benzene (421 mg, 2.32 mmol, 1.00 equiv) and triphenylphosphine (669 mg, 2.55 mmol, 1.10 equiv) were dissolved in CHCl$_3$ (4.65 mL) at room temperature. CS$_2$ (1.19 mL, 19.7 mmol, 8.50 mmol) was added and it was stirred for 1 h. The mixture was directly subjected to flash chromatography on silica (2% EtOAc in hexanes) to afford 1-(chloromethyl)-2-(isothiocyanatomethyl)benzene (114 mg, 0.577 mmol, 24.9% yield) as a colorless oil. HRMS (EI+) 197.0054 (M$^+$).

c) 5-tert-Butyl-7-(3,3-difluoropyrrolidin-1-yl)-3-{[2-(isothiocyanatomethyl)phenyl]methyl}-3H-[1,2,3]triazolo[4,5-d]pyrimidine In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from 5-tert-butyl-7-(3,3-difluoropyrrolidin-1-yl)-3H-[1,2,3]triazolo[4,5-d]pyrimidine (CAS 1438465-59-8, 56 mg, 0.20 mmol) and 1-(chloromethyl)-2-(isothiocyanatomethyl)benzene and isolated as colorless oil (37 mg, 0.083 mmol, 42% yield). HRMS (ESI+) 444.1772 (M+H$^+$).

Example 5

(3S)-1-(5-tert-Butyl-3-{[2-(isothiocyanatomethyl)phenyl]methyl}-3H-[1,2,3]triazolo[4,5-d]pyrimidin-7-yl)pyrrolidin-3-ol

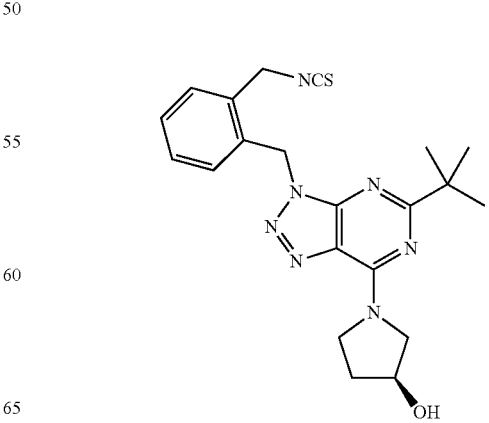

In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from (3S)-1-(5-tert-butyl-3H-triazolo[4,5-d]pyrimidin-7-yl)pyrrolidin-3-ol (CAS 1433946-74-7, 57 mg, 0.22 mmol, 1.0 equiv) and 1-(chloromethyl)-2-(isothiocyanatomethyl)benzene and isolated as colorless oil (45 mg, 0.106 mmol, 49% yield). HRMS (ESI+) 424.1916 (M+H$^+$).

Example 6

5-tert-Butyl-7-(3,3-difluoropyrrolidin-1-yl)-3-[(2-isothiocyanatophenyl)methyl]-3H-[1,2,3]triazolo[4,5-d]pyrimidine

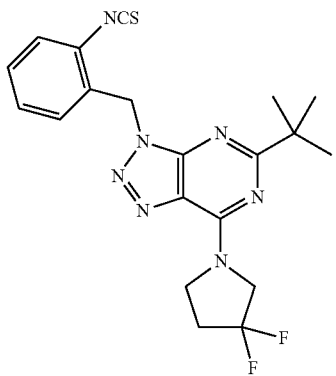

In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from 5-tert-butyl-7-(3,3-difluoropyrrolidin-1-yl)-3H-[1,2,3]triazolo[4,5-d]pyrimidine (CAS 1438465-59-8, 45 mg, 0.16 mmol) and 1-bromomethyl-2-isothiocyanatobenzene (CAS 108288-40-0) and isolated as colorless oil (20 mg, 0.047 mmol, 29% yield). HRMS (ESI+) 430.1621 (M+H$^+$).

Example 7

2-{[5-tert-Butyl-7-(3,3-difluoropyrrolidin-1-yl)-3H-[1,2,3]triazolo[4,5-d]pyrimidin-3-yl]methyl}benzene-1-sulfonyl fluoride

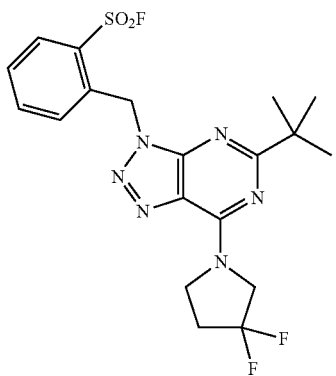 [SMILES: CC(C)(C)c1nc(N2CCC(F)(F)C2)c2nnn(Cc3ccccc3S(=O)(=O)F)c2n1]

In analogy to the procedure described for the synthesis of 2-[[5-tert-butyl-7-[(3S)-3-hydroxypyrrolidin-1-yl]triazolo[4,5-d]pyrimidin-3-yl]methyl]benzenesulfonyl fluoride (example 1, step b), the title compound was prepared from 5-tert-butyl-7-(3,3-difluoropyrrolidin-1-yl)-3H-[1,2,3]triazolo[4,5-d]pyrimidine (CAS 1438465-59-8, 60 mg, 0.21 mmol) and 2-(bromomethyl)benzene-1-sulfonyl fluoride and isolated as colorless oil (33 mg, 0.072 mmol, 34% yield). HRMS (ESI+) 455.1470 (M+H$^+$).

Example 8

1-{5-tert-Butyl-3-[(2-chlorophenyl)methyl]-3H-[1,2,3]triazolo[4,5-d]pyrimidin-7-yl}pyrrolidine-3-thiol

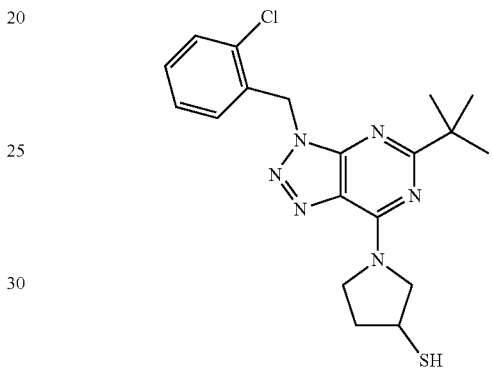

a) 1-(5-(tert-Butyl)-3-(2-chlorobenzyl)-3H-[1,2,3]triazolo[4,5-d]pyrimidin-7-yl)pyrrolidin-3-yl methanesulfonate

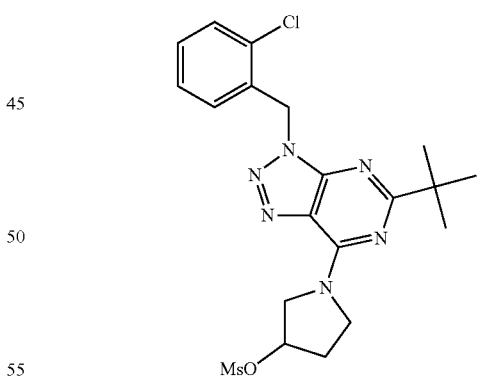

1-[5-tert-Butyl-3-(2-chloro-benzyl)-3H-[1,2,3]triazolo[4,5-d]pyrimidin-7-yl]-pyrrolidin-3-ol (CAS 1433362-08-3, 154 mg, 0.398 mmol, 1.00 equiv) and NEt$_3$ (111 µL, 0.796 mmol, 2.00 equiv) were dissolved in CH$_2$Cl$_2$ (1.80 mL) and cooled to 0° C. Then MsCl (62 µL, 0.80 mmol, 2.0 equiv) was added as a solution in CH$_2$Cl$_2$ (0.40 mL). After 40 min, the reaction mix was diluted with water and extracted with CH$_2$Cl$_2$. The combined organics were concentrated and the residue subjected to flash chromatography on silica (5%

EtOAc in CH$_2$Cl$_2$) to afford 1-(5-(tert-butyl)-3-(2-chlorobenzyl)-3H-[1,2,3]triazolo[4,5-d]pyrimidin-7-yl)pyrrolidin-3-yl methanesulfonate (170 mg, 0.366 mmol, 92% yield) as colorless oil. HRMS (ESI+) 465.1469 (M+H$^+$).

b) S-(1-(5-(tert-Butyl)-3-(2-chlorobenzyl)-3H-[1,2,3]triazolo[4,5-d]pyrimidin-7-yl)pyrrolidin-3-yl) ethanethioate

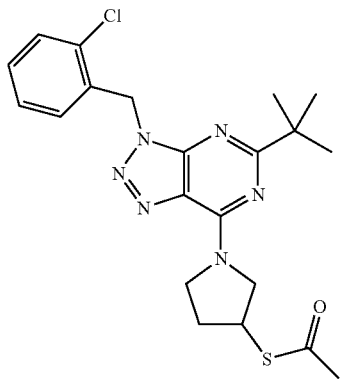 [SMILES: CC(=O)SC1CCN(c2nc(C(C)(C)C)nc3c2nnn3Cc2ccccc2Cl)C1]

1-(5-(tert-Butyl)-3-(2-chlorobenzyl)-3H-[1,2,3]triazolo[4,5-d]pyrimidin-7-yl)pyrrolidin-3-yl methanesulfonate (361 mg, 0.776 mmol, 1.00 equiv) was dissolved in DMF (7.76 mL), potassium thioacetate (887 mg, 7.76 mmol, 10.0 equiv) was added and it was stirred at 50° C. for 2 h. After cooling to room temperature, the mix was diluted with water and extracted with EtOAc. The organics were washed with dilute aq. NaHCO$_3$ and brine, dried over MgSO$_4$, filtered and concentrated. Flash chromatography on silica (gradient 10% to 20% EtOAc in hexanes) afforded S-(1-(5-(tert-butyl)-3-(2-chlorobenzyl)-3H-[1,2,3]triazolo[4,5-d]pyrimidin-7-yl)pyrrolidin-3-yl) ethanethioate (345 mg, 0.735 mmol, 95% yield) as colorless solid. HRMS (ESI+) 445.1579 (M+H$^+$).

c) 1-{5-tert-Butyl-3-[(2-chlorophenyl)methyl]-3H-[1,2,3]triazolo[4,5-d]pyrimidin-7-yl}pyrrolidine-3-thiol S-(1-(5-(tert-Butyl)-3-(2-chlorobenzyl)-3H-[1,2,3]triazolo[4,5-d]pyrimidin-7-yl)pyrrolidin-3-yl) ethanethioate (109 mg, 0.245 mmol, 1.00 equiv) was dissolved in a 1:1 mixture of MeOH and THF (2.40 mL). K$_2$CO$_3$ (203 mg, 1.47 mmol, 6 equiv) was added and it was stirred for 15 min. The reaction mix was diluted with water (50 mL) and extracted with EtOAc (3×20 mL). The organics were washed with brine, dried over MgSO$_4$, filtered and concentrated. Flash chromatography on silica (CH$_2$Cl$_2$:hexanes:MeOH 50:50:1) afforded 1-{5-tert-butyl-3-[(2-chlorophenyl)methyl]-3H-[1,2,3]triazolo[4,5-d]pyrimidin-7-yl}pyrrolidine-3-thiol (86 mg, 0.21 mmol, 87% yield) as colorless oil. HRMS (ESI+) 403.1468 (M+H$^+$).

Example 9

1-{5-tert-Butyl-3-[(2-chlorophenyl)methyl]-3H-[1,2,3]triazolo[4,5-d]pyrimidin-7-yl}azetidine-3-thiol

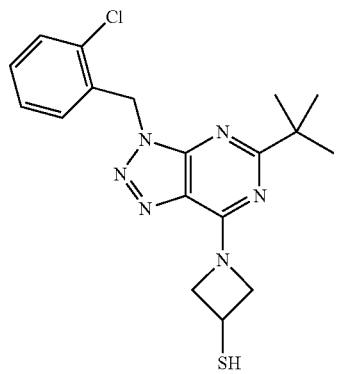 [SMILES: CC(C)(C)c1nc(N2CC(S)C2)c2nnn(Cc3ccccc3Cl)c2n1]

A suspension of 5-(tert-butyl)-7-chloro-3-(2-chlorobenzyl)-3H-[1,2,3]triazolo[4,5-d]pyrimidine (CAS 1433362-85-6, 20 mg, 59.5 µmol), azetidine-3-thiol hydrochloride (CAS 179337-60-1, 11.2 mg, 89.2 µmol) and DIPEA (23.1 mg, 30.5 µL, 178 µmol) in acetonitrile (3 mL) was stirred at ambient temperature for 18 h. The solvent was removed under reduced pressure and the residue purified by preparative TLC (silica gel, 2.0 mm, 3:1 Heptane:EtOAc) to give the title compound (11 mg, 48%) as a colorless semisolid oil. HRMS (ESI+) 389.1297 (M+H$^+$).

Example 10

(3S)-1-{5-tert-Butyl-3-[(4-methyl-1,2,5-oxadiazol-3-yl)methyl]-3H-[1,2,3]triazolo[4,5-d]pyrimidin-7-yl}pyrrolidine-3-thiol or enantiomer

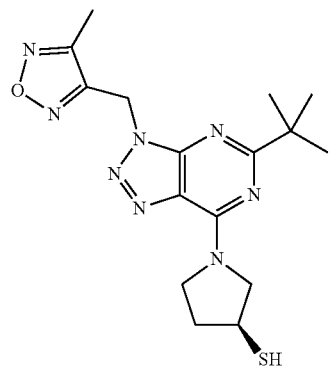 [SMILES: Cc1nonc1Cn1nnc2c(N3CC[C@H](S)C3)nc(C(C)(C)C)nc21]

a) 3-((5-(tert-Butyl)-7-chloro-3H-[1,2,3]triazolo[4,5-d]pyrimidin-3-yl)methyl)-4-methyl-1,2,5-oxadiazole

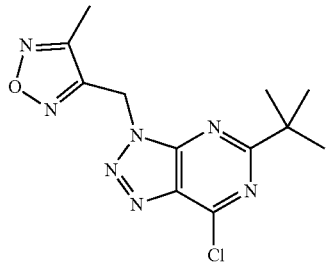 [SMILES: Cc1nonc1Cn1nnc2c(Cl)nc(C(C)(C)C)nc21]

5-(tert-Butyl)-3-((4-methyl-1,2,5-oxadiazol-3-yl)methyl)-3H-[1,2,3]triazolo[4,5-d]pyrimidin-7(4H)-one (CAS 1919022-49-3, 235 mg, 0.812 mmol, 1.00 equiv) and one drop of DMF were dissolved in CH$_2$Cl$_2$ (2.71 mL). Oxalyl chloride (80 µL, 0.89 mmol, 1.1 equiv) was added and the reaction mix was stirred overnight at room temperature. Celite was added and the solvent was removed. Flash chromatography on silica (0.5% MeOH in CH$_2$Cl$_2$) afforded 3-((5-(tert-butyl)-7-chloro-3H-[1,2,3]triazolo[4,5-d]pyrimidin-3-yl)methyl)-4-methyl-1,2,5-oxadiazole (230 mg, 0.757 mmol, 92% yield) as colorless solid. HRMS (MALDI+) 308.1021 (M+).

b) Pyrrolidin-3-yl methanesulfonate hydrochloride

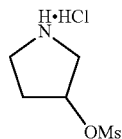

3-Methanesulfonyloxy-pyrrolidine-1-carboxylic acid tert-butyl ester (CAS 141699-57-2, 768 mg, 2.89 mmol, 1.00 equiv) was dissolved in Et$_2$O (8.7 mL) and HCl (4 M in dioxane, 8.68 mL, 17.4 mmol, 6 equiv) was added. The mixture was stirred overnight, concentrated and the residue was used without further purification.

c) 1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl methanesulfonate

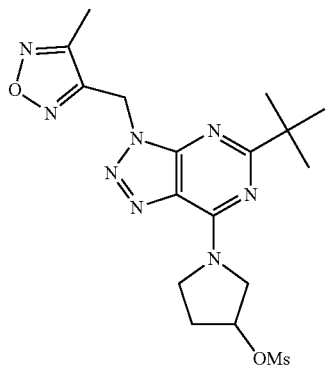 [SMILES: Cc1nonc1Cn1nnc2c(N3CCC(OS(C)(=O)=O)C3)nc(C(C)(C)C)nc21]

3-((5-(tert-Butyl)-7-chloro-3H-[1,2,3]triazolo[4,5-d]pyrimidin-3-yl)methyl)-4-methyl-1,2,5-oxadiazole (300 mg, 0.98 mmol, 1.00 equiv) was dissolved in CH$_2$Cl$_2$ (4.87 mL) at room temperature and pyrrolidin-3-yl methanesulfonate hydrochloride (216 mg, 1.07 mmol, 1.10 equiv) was added. Then NEt$_3$ (272 µL, 1.95 mmol, 2.00 equiv) was added and it was stirred for 30 minutes. Celite was added and the solvent evaporated. Flash chromatography on silica (50% EtOAc in hexanes) afforded 1-(5-(tert-butyl)-3-((4-methyl-1,2,5-oxadiazol-3-yl)methyl)-3H-[1,2,3]triazolo[4,5-d]pyrimidin-7-yl)pyrrolidin-3-yl methanesulfonate (426 mg, 0.89 mmol, 91% yield) as colorless oil. HRMS (ESI+) 437.1715 (M+H+).

d) S-(1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl) ethanethioate

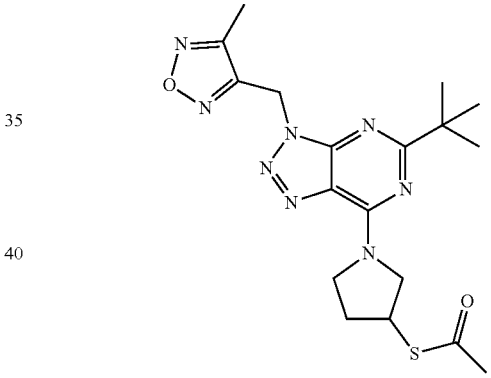

1-(5-(tert-Butyl)-3-((4-methyl-1,2,55-oxadiazol-3-yl)methyl)-3H-[1,2,3]triazolo[4,5-d]pyrimidin-7-yl)pyrrolidin-3-yl methanesulfonate (147 mg, 0.337 mmol, 1.0 equiv) and potassium thioacetate (385 mg, 3.37 mmol, 10.0 equiv) were combined with DMF (1.8 mL) and heated to 50° C. for 2 h. The reaction mixture was cooled to room temperature and diluted with EtOAc (50 mL). The organic phase was washed with water (10 mL), 5% aq. LiCl (10 mL) and brine (10 mL), dried over MgSO$_4$, filtered and concentrated. Flash chromatography on silica (15% EtOAc in hexanes) afforded S-(1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl) ethanethioate (107 mg, 0.257 mmol, 76% yield). HRMS (ESI+) 417.1813 (M+H+).

e) S-[(3S)-1-[5-tert-Butyl-3-[(4-methyl-1,2,5-oxadiazol-3-yl)methyl]triazolo[4,5-d]pyrimidin-7-yl]pyrrolidin-3-yl]ethanethioate

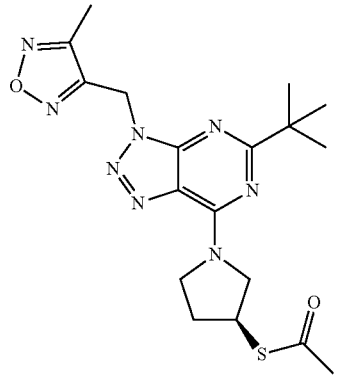 [SMILES: CC(=O)S[C@H]1CCN(c2nc(C(C)(C)C)nc3c2nnn3Cc2nonc2C)C1]

Racemic S-(1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl) ethanethioate (107 mg, 0.257 mmol) was subjected to separation by chiral HPLC to yield the title compound (25 mg, 0.06 mmol, 23%).

f) (3S)-1-{5-tert-Butyl-3-[(4-methyl-1,2,5-oxadiazol-3-yl)methyl]-3H-[1,2,3]triazolo[4,5-d]pyrimidin-7-yl}pyrrolidine-3-thiol A mixture of S-[(3S)-1-[5-tert-butyl-3-[(4-methyl-1,2,5-oxadiazol-3-yl)methyl]triazolo[4,5-d]pyrimidin-7-yl]pyrrolidin-3-yl]ethanethioate (25 mg, 0.06 mmol) and K$_2$CO$_3$ (45.6 mg, 330 μmol) in THF (3 mL), water (1 mL) and methanol (1 mL) was stirred at ambient temperature for 72 h. The reaction mixture was poured into water (30 mL) and extracted with EtOAc (2×30 mL). The combined extracts were washed with water/brine (1:1), dried over Na$_2$SO$_4$ and concentrated under reduced pressure. The crude material was purified by preparative TLC (silica gel, 1.0 mm, 1:1 heptane/EtOAc) to yield the title compound (12 mg, 52% yield) as colorless solid. MS(ESI): m/z=374.1 [M]$^+$ Example 11

(3R)-1-{5-tert-Butyl-3-[(4-methyl-1,2,5-oxadiazol-3-yl)methyl]-3H-[1,2,3]triazolo[4,5-d]pyrimidin-7-yl}pyrrolidine-3-thiol or enantiomer

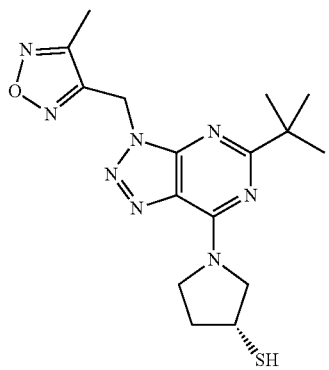 [SMILES: Cc1nonc1Cn1nnc2c(N3CC[C@@H](S)C3)nc(C(C)(C)C)nc21]

a) S-[(3R)-1-[5-tert-Butyl-3-[(4-methyl-1,2,5-oxadiazol-3-yl)methyl]triazolo[4,5-d]pyrimidin-7-yl]pyrrolidin-3-yl]ethanethioate

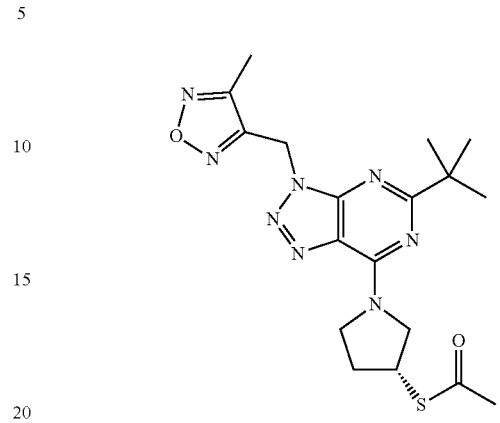

Racemic S-(1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl) ethanethioate (107 mg, 0.257 mmol) was subjected to separation by chiral HPLC to yield the title compound (33 mg, 0.08 mmol, 31%).

b) (3R)-1-{5-tert-Butyl-3-[(4-methyl-1,2,5-oxadiazol-3-yl)methyl]-3H-[1,2,3]triazolo[4,5-d]pyrimidin-7-yl}pyrrolidine-3-thiol In analogy to the procedure described in example 10 (step f), S-[(3R)-1-[5-tert-butyl-3-[(4-methyl-1,2,5-oxadiazol-3-yl)methyl]triazolo[4,5-d]pyrimidin-7-yl]pyrrolidin-3-yl] ethanethioate was hydrolyzed to obtain the title compound (14 mg, 61%) as colorless solid. MS(ESI): m/z=374.1 [M]$^+$ Example 12

(3S)-1-{5-tert-Butyl-3-[(2-chlorophenyl)methyl]-3H-[1,2,3]triazolo[4,5-d]pyrimidin-7-yl}pyrrolidine-3-thiol or enantiomer

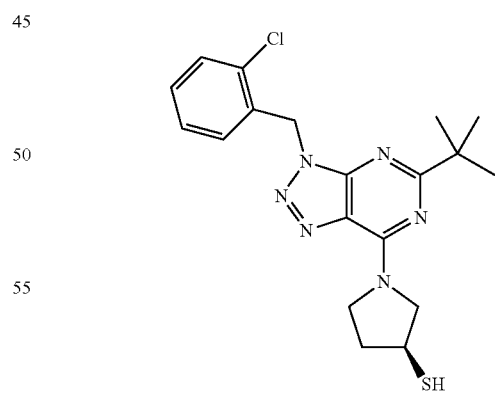

In analogy to the procedure described for the synthesis of (3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol (example 10, steps a, c-f) the title compound (11 mg, 60%) was prepared as colorless solid from 5-tert-butyl-7-chloro-3-(2-chlorobenzyl)-3H-[1,2,3]triazolo[4,5-d]pyrimidine (CAS 1433362-85-6). $^1$H NMR (300 MHz, CDCl$_3$)

δ=1.20-1.32 (m, 1H) 1.36 (s, 9H) 2.17-2.50 (m, 2H) 3.87-4.20 (m, 2H) 4.25-4.61 (m, 2H) 5.86 (s, 2H) 7.14-7.25 (m, 3H) 7.38-7.41 (m, 1H).

Example 13

(3R)-1-{5-tert-Butyl-3-[(2-chlorophenyl)methyl]-3H-[1,2,3]triazolo[4,5-d]pyrimidin-7-yl}pyrrolidine-3-thiol or enantiomer

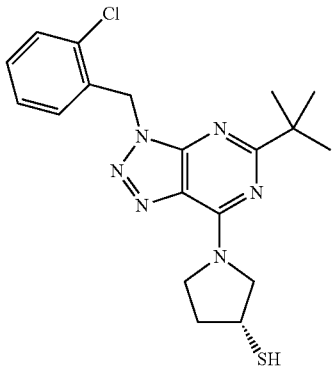 [SMILES: CC(C)(C)c1nc(N2CC[C@@H](S)C2)c2nnn(Cc3ccccc3Cl)c2n1]

In analogy to the procedure described for the synthesis of (3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol (example 10, steps c-f) the title compound (12 mg, 60%) was prepared as colorless solid from 5-tert-butyl-7-chloro-3-(2-chlorobenzyl)-3H-[1,2,3]triazolo[4,5-d]pyrimidine (CAS 1433362-85-6). $^1$H NMR (300 MHz, CDCl$_3$) δ=1.21-1.32 (m, 1H) 1.36 (s, 9H) 2.19-2.39 (m, 2H) 3.87-4.22 (m, 2H) 4.27-4.61 (m, 2H) 5.86 (s, 2H) 7.13-7.25 (m, 3H) 7.38-7.40 (m, 1H).

Example 14

7-(3-Azidopyrrolidin-1-yl)-5-tert-butyl-3-[(4-methyl-1,2,5-oxadiazol-3-yl)methyl]-3H-[1,2,3]triazolo[4,5-d]pyrimidine

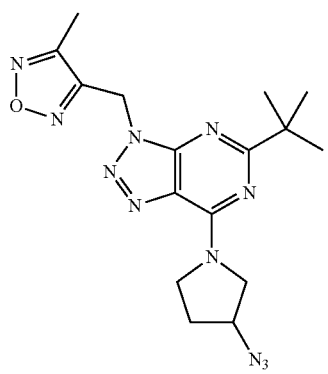 [SMILES: Cc1nonc1Cn1nnc2c(N3CCC(N=[N+]=[N-])C3)nc(C(C)(C)C)nc21]

1-(5-(tert-Butyl)-3-((4-methyl-1,2,5-oxadiazol-3-yl)methyl)-3H-[1,2,3]triazolo[4,5-d]pyrimidin-7-yl)pyrrolidin-3-yl methanesulfonate (194 mg, 0.444 mmol, 1.00 equiv) was dissolved in DMF (3.70 mL) and NaN$_3$ (144 mg, 2.22 mmol, 5 equiv) was added. The reaction mixture was stirred at 90° C. for 1 h. After cooling to room temperature, the mixture was diluted with water and extracted with EtOAc. The combined organics were washed with brine, dried over MgSO$_4$, filtered and concentrated. Flash chromatography on silica (20% EtOAc in hexanes) afforded 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine (153 mg, 0.399 mmol, 90% yield) as colorless oil. HRMS (ESI+) 384.2005 (M+H$^+$).

Example 15

5-tert-Butyl-3-[(2-chlorophenyl)methyl]-7-(3-isothiocyanatopyrrolidin-1-yl)-3H-[1,2,3]triazolo[4,5-d]pyrimidine

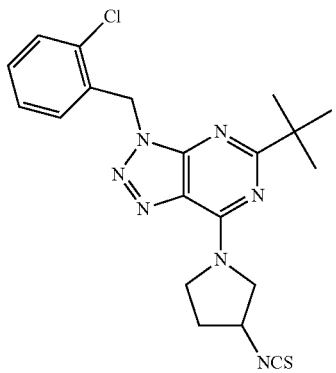

a) 1-(5-(tert-Butyl)-3-(2-chlorobenzyl)-3H-[1,2,3]triazolo[4,5-d]pyrimidin-7-yl)pyrrolidin-3-amine

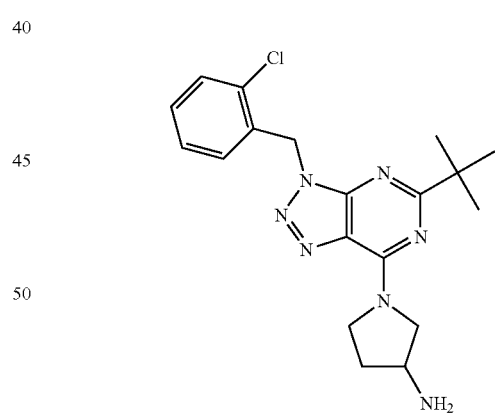

7-(3-Azidopyrrolidin-1-yl)-5-tert-butyl-3-[(4-methyl-1,2,5-oxadiazol-3-yl)methyl]-3H-[1,2,3]triazolo[4,5-d]pyrimidine (32 mg, 0.078 mmol, 1.0 equiv), water (28 μL, 1.6 mmol, 20 equiv) and PPh$_3$ (41 mg, 0.16 mmol, 2.0 equiv) were combined with THF (710 μL) and stirred at 50° C. for 1.5 h. Celite was added and the solvent was removed. Flash chromatography on silica (10% MeOH in CH$_2$Cl$_2$) afforded 1-(5-(tert-butyl)-3-(2-chlorobenzyl)-3H-[1,2,3]triazolo[4,5-d]pyrimidin-7-yl)pyrrolidin-3-amine (21 mg, 0.054 mmol, 70% yield) as colorless solid. HRMS (ESI+) 386.1857 (M+H$^+$).

b) 5-tert-Butyl-3-[(2-chlorophenyl)methyl]-7-(3-isothiocyanatopyrrolidin-1-yl)-3H-[1,2,3]triazolo[4,5-d]pyrimidine 1-(5-(tert-Butyl)-3-(2-chlorobenzyl)-3H-[1,2,3]triazolo[4,5-d]pyrimidin-7-yl)pyrrolidin-3-amine (12 mg, 0.031 mmol, 1.0 equiv) was combined with N,N'-thiocarbonyldiimidazole (11 mg, 0.062 mmol, 2.0 equiv) in THF (155 µL) and stirred overnight. Celite was added and the solvent was removed. Flash chromatography on silica afforded 5-tert-butyl-3-[(2-chlorophenyl)methyl]-7-(3-isothiocyanatopyrrolidin-1-yl)-3H-[1,2,3]triazolo[4,5-d]pyrimidine (6.5 mg, 0.015 mmol, 49% yield) as colorless oil. $^1$H NMR (300 MHz, Chloroform-d) δ=7.43-7.38 (m, 1H), 7.27-7.17 (m, 3H), 5.87 (s, 2H), 4.64-4.47 (m, 2H), 4.40-4.27 (m, 1H), 4.17-4.04 (m, 1H), 4.02-3.92 (m, 1H), 2.55-2.27 (m, 2H), 1.37 (s, 9H).

Example 16

5-tert-Butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine

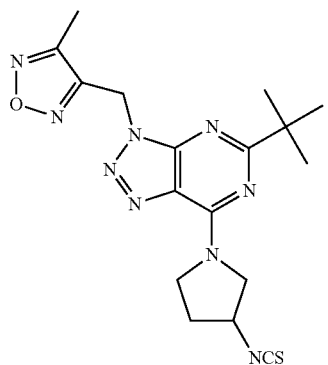

7-(3-Azidopyrrolidin-1-yl)-5-tert-butyl-3-[(4-methyl-1,2,5-oxadiazol-3-yl)methyl]-3H-[1,2,3]triazolo[4,5-d]pyrimidine (50 mg, 0.13 mmol, 1.0 equiv), PPh$_3$ (41 mg, 0.16 mmol, 1.2 equiv) were dissolved in THF (650 µL) and CS$_2$ (79 µL, 1.3 mmol, 10 equiv) was added. The reaction mix was stirred overnight at room temperature. Celite was added and the solvent was removed. Flash chromatography on silica (20% EtOAc in hexanes) afforded 5-tert-butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine (33 mg, 0.083 mmol, 63% yield) as colorless oil. HRMS (ESI+) 400.1665 (M+H$^+$).

Example 17

7-(3-Azidopyrrolidin-1-yl)-5-tert-butyl-3-[(2-chlorophenyl)methyl]-3H-[1,2,3]triazolo[4,5-d]pyrimidine

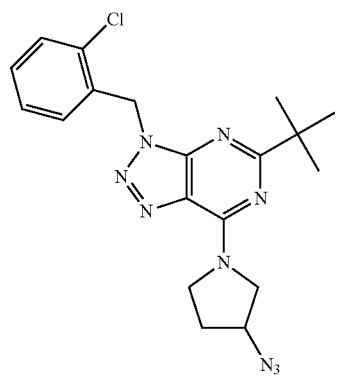 [SMILES: CC(C)(C)c1nc(N2CCC(N=[N+]=[N-])C2)c2nnn(Cc3ccccc3Cl)c2n1]

In analogy to the procedure described for the synthesis of 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine (Example 14) the title compound was prepared from 1-(5-(tert-butyl)-3-(2-chlorobenzyl)-3H-[1,2,3]triazolo[4,5-d]pyrimidin-7-yl)pyrrolidin-3-yl methanesulfonate and isolated as colorless oil. HRMS (ESI+) 412.1763 (M+H$^+$).

Example 18

5-[Difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine

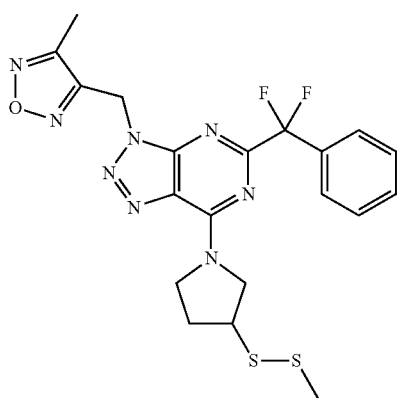 [SMILES: CSSC1CCN(c2nc(C(F)(F)c3ccccc3)nc3c2nnn3Cc2nonc2C)C1]

a) 5-Amino-1-((4-methyl-1,2,5-oxadiazol-3-yl)methyl)-1H-1,2,3-triazole-4-carboxamide

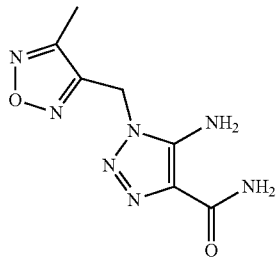 [SMILES: Cc1nonc1Cn1nnc(C(N)=O)c1N]

5-Amino-1-(2-chlorobenzyl)-1H-1,2,3-triazole-4-carboxamide (CAS 93444-91-8, 2.01 g, 15.2 mmol, 1.0 equiv) and DIPEA (0.27 mL, 1.52 mmol, 0.1 equiv) were dissolved in DMSO (9.7 mL) and NaN$_3$ (1.04 g, 15.9 mmol, 1.05 equiv) was added in portions. The reaction mixture was stirred overnight at room temperature. In a second reaction vessel, cyanoacetamide (1.91 g, 22.8 mmol, 1.5 equiv) was dissolved in DMSO (7.8 mL) and water (1.2 mL). Then 32% aqueous NaOH (1.4 mL, 15.2 mL, 1.0 equiv) was added slowly (exothermic) and the mixture was stirred for 15 min. The previously prepared solution of the organoazide was added slowly (exothermic) and the reaction mixture was stirred overnight at room temperature. Water (20 mL) was added slowly (exothermic). The resulting suspension was cooled to 0° C. and stirred for 1 h. Filtration (washing with water, 2×5 mL) and drying afforded 5-amino-1-((4-methyl-1,2,5-oxadiazol-3-yl)methyl)-1H-1,2,3-triazole-4-carboxamide (2.0 g, 9.0 mmol, 59% yield) as beige solid.

b) 5-(Difluoro(phenyl)methyl)-3-((4-methyl-1,2,5-oxadiazol-3-yl)methyl)-3H-[1,2,3]triazolo[4,5-d]pyrimidin-7(4H)-one

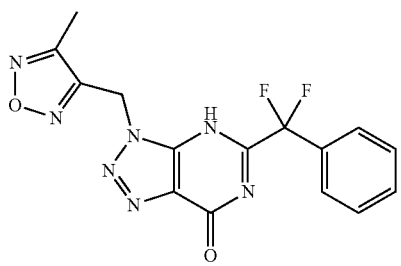 [SMILES: Cc1nonc1Cn1nnc2c(=O)nc(C(F)(F)c3ccccc3)[nH]c21]

5-Amino-1-((4-methyl-1,2,5-oxadiazol-3-yl)methyl)-1H-1,2,3-triazole-4-carboxamide (1.50 g, 6.72 mmol, 1.00 equiv), 2,2-difluoro-2-phenylacetonitrile (1.60 g, 10.5 mmol, 1.56 equiv) and K$_2$CO$_3$ (4.64 g, 33.6 mmol, 5.00 equiv) were combined with DMF (19.2 ml) and heated to 90° C. overnight. The reaction mix was cooled to room temperature and poured into icewater. Aq. HCl (1 M) was added until pH=3 and it was extracted with EtOAc (3×100 mL). The combined organics were washed with 5% aq. LiCl and brine, dried over MgSO$_4$, filtered and concentrated to leave a brown oil. Trituration of the residue with 2-PrOH and filtration afforded a pale yellow solid (1.45 g). The filtrate was concentrated and chromatographed on silica (CH$_2$Cl$_2$:acetone 9:1+1% MeOH). The fractions containing product were combined, concentrated and the residue again triturated with 2-PrOH to give another crop of 5-(difluoro(phenyl)methyl)-3-((4-methyl-1,2,5-oxadiazol-3-yl)methyl)-3H-[1,2,3]triazolo[4,5-d]pyrimidin-7(4H)-one (combined 1.72 g, 4.79 mmol, 71% yield). HRMS (ESI+) 360.1015 (M+H$^+$).

c) 3-((7-Chloro-5-(difluoro(phenyl)methyl)-3H-[1,2,3]triazolo[4,5-d]pyrimidin-3-yl)methyl)-4-methyl-1,2,5-oxadiazole

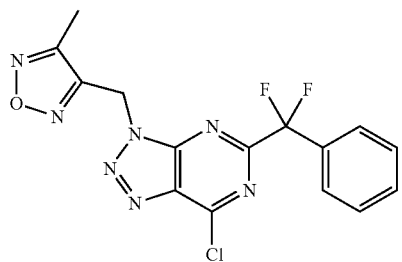 [SMILES: Cc1nonc1Cn1nnc2c(Cl)nc(C(F)(F)c3ccccc3)nc21]

5-(Difluoro(phenyl)methyl)-3-((4-methyl-1,2,5-oxadiazol-3-yl)methyl)-3H-[1,2,3]triazolo[4,5-d]pyrimidin-7(4H)-one (112 mg, 0.237 mmol, 1.00 equiv) was dissolved in CH$_2$Cl$_2$ (790 µL) and one drop of DMF was added. Oxalyl chloride (42 µL, 0.474 mmol, 2.00 equiv) was added dropwise and the mixture was heated to reflux for 1.5 h. The reaction mix was cooled to room temperature and diluted with EtOAc (30 mL). The organic phase was washed with water and brine, dried over MgSO$_4$, filtered and concentrated. Flash chromatography on silica (20% EtOAc in hexanes) afforded 3-((7-chloro-5-(difluoro(phenyl)methyl)-3H-[1,2,3]triazolo[4,5-d]pyrimidin-3-yl)methyl)-4-methyl-1,2,5-oxadiazole (80 mg, 0.21 mmol, 89% yield) as a colorless oil. HRMS (ESI+) 378.0677 (M+H$^+$).

d) 1-(5-(Difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl methanesulfonate

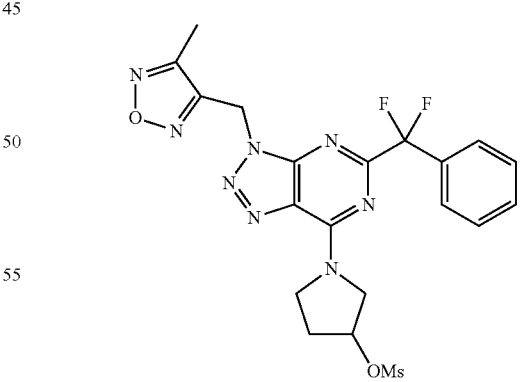

3-((7-Chloro-5-(difluoro(phenyl)methyl)-3H-[1,2,3]triazolo[4,5-d]pyrimidin-3-yl)methyl)-4-methyl-1,2,5-oxadiazole (151 mg, 0.401 mmol, 1.00 equiv) was combined with pyrrolidin-3-yl methanesulfonate hydrochloride (97 mg, 0.48 mmol, 1.2 equiv) and CH$_2$Cl$_2$ (1.34 mL). NEt$_3$ (112 µL, 0.802 mmol, 2.00 equiv) was added and the mixture was stirred for 30 minutes. Celite was added and the solvent was removed. Flash chromatography on silica (50% EtOAc in hexanes) afforded 1-(5-(difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl methanesulfonate (165 mg, 0.326 mmol, 81% yield). HRMS (ESI+) 507.1374 (M+H+).

e) S-(1-(5-(Difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl) ethanethioate

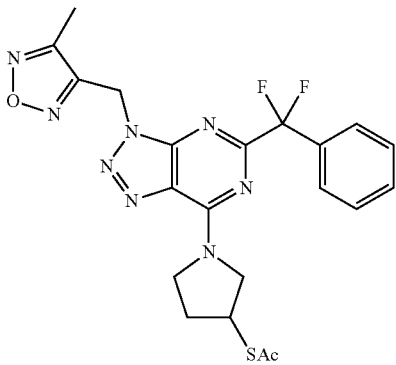

In analogy to the procedure described for the synthesis of S-(1-(5-(tert-butyl)-3-((4-methyl-1,2,5-oxadiazol-3-yl)methyl)-3H-[1,2,3]triazolo[4,5-d]pyrimidin-7-yl)pyrrolidin-3-yl) ethanethioate (example 10, step f) the title compound was synthesized from 1-(5-(difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl methanesulfonate (92 mg, 0.182 mmol) and isolated as slightly yellow wax (80 mg, 0.164 mmol, 91% yield). $^1$H NMR (300 MHz, Chloroform-d) δ=7.70-7.62 (m, 2H), 7.42-7.35 (m, 3H), 5.90 (s, 2H), 4.61 (dd, J=12.2, 6.2, 0.5H), 4.34-4.08 (m, 3H), 3.89 (td, J=7.0, 2.9, 1H), 3.76 (dd, J=12.5, 4.7, 0.5H), 2.63-2.39 (m, 1H), 2.36 (s, 1.5H), 2.34 (s, 1.5H), 2.34 (s, 3H), 2.24-2.01 (m, 1H), mixture of rotamers.

f) 1-(5-(Difluoro(phenyl)methyl)-3-((4-methyl-1,2,5-oxadiazol-3-yl)methyl)-3H-[1,2,3]triazolo[4,5-d]pyrimidin-7-yl)pyrrolidine-3-thiol

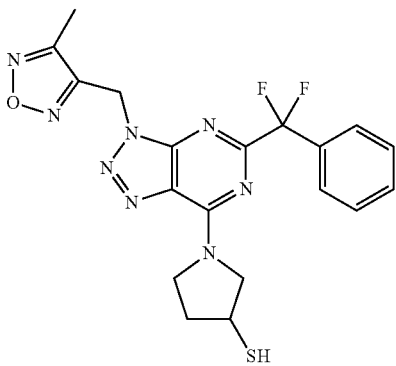 [SMILES: Cc1nonc1Cn1nnc2c(N3CCC(S)C3)nc(C(F)(F)c3ccccc3)nc21]

S-(1-(5-(Difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl) ethanethioate (35 mg, 0.072 mmol, 1.0 equiv) was dissolved in THF (700 µL) and cooled to 0° C. NaOMe (1 M in MeOH, 94 µL, 0.94 mmol, 1.3 equiv) was added and it was stirred for 1 h. Sat. aq. NH4Cl was added and the mix was extracted with EtOAc. The combined organics were dried over MgSO4, filtered and concentrated. Flash chromatography on silica (25% EtOAc in hexanes) afforded 1-(5-(difluoro(phenyl)methyl)-3-((4-methyl-1,2,5-oxadiazol-3-yl)methyl)-3H-[1,2,3]triazolo[4,5-d]pyrimidin-7-yl)pyrrolidine-3-thiol (22 mg, 0.049 mmol, 69% yield) as colorless solid. HRMS (ESI+) 445.1371 (M+H+).

g) 5-[Difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine To a solution of 1-(5-(difluoro(phenyl)methyl)-3-((4-methyl-1,2,5-oxadiazol-3-yl)methyl)-3H-[1,2,3]triazolo[4,5-d]pyrimidin-7-yl)pyrrolidine-3-thiol (19 mg, 0.043 mmol, 1.0 equiv) in NaH2PO4-buffer (0.5 M, 260 µL) and EtOH (450 µL) was added methyl methanethiosulfonate (160 al, 0.056 mmol, 1.3 equiv, diluted in EtOH 1:30). The mixture was stirred for 12 hours. Additional methyl methanethiosulfonate (40 al, 0.011 mmol, 0.3 equiv) was added. The mixture was stirred for 2 h. EtOAc (100 mL) was added. The mix was washed with water and brine, dried over MgSO4 and concentrated. Flash chromatography on silica (20% EtOAc in hexanes) afforded 5-[difluoro(phenyl)methyl]-7-[3-(methyldisulfanyl)pyrrolidin-1-yl]-3-[(4-methyl-1,2,5-oxadiaazol-3-yl)methyl]-3H-[1,2,3]triazolo[4,5-d]pyrimidine (14 mg, 0.029 mmol, 67% yield) as colorless oil. HRMS (ESI+) 491.1245 (M+H+).

Example 19

3-[(2-Chlorophenyl)methyl]-5-[difluoro(phenyl)methyl]-7-[3-(methyldisulfanyl)pyrrolidin-1-yl]-3H-[1,2,3]triazolo[4,5-d]pyrimidine

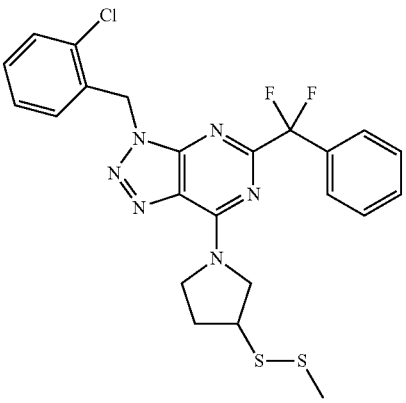 [SMILES: CSSC1CCN(c2nc(C(F)(F)c3ccccc3)nc3c2nnn3Cc2ccccc2Cl)C1]

In analogy to the procedure described for the synthesis of 5-[difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine (Example 18, steps b-g) the title compound was prepared from 5-amino-1-(2-chlorobenzyl)-1H-1,2,3-triazole-4-carboxamide (CAS 93444-91-8) and isolated as colorless oil. HRMS (ESI+) 519.0995 (M+H+).

Example 20

7-(3-Azidopyrrolidin-1-yl)-5-[difluoro(phenyl)methyl]-3-[(4-methyl-1,2,5-oxadiazol-3-yl)methyl]-3H-[1,2,3]triazolo[4,5-d]pyrimidine

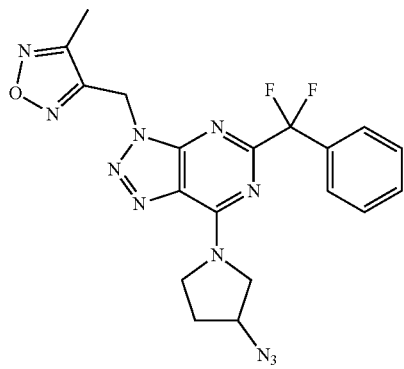 [SMILES: Cc1nonc1Cn1nnc2c(N3CCC(N=[N+]=[N-])C3)nc(C(F)(F)c3ccccc3)nc21]

In analogy to the procedure described for the synthesis of 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine (example 14) the title compound was prepared from 1-(5-(difluoro(phenyl)methyl)-3-((4-methyl-1,2,5-oxadiazol-3-yl)methyl)-3H-[1,2,3]triazolo[4,5-d]pyrimidin-7-yl)pyrrolidin-3-yl methanesulfonate (66 mg, 0.13 mmol, 1.0 equiv) and isolated as colorless solid (54 mg, 0.12 mmol, 91% yield). HRMS (ESI+) 454.1661 (M+H⁺).

Example 21

7-(3-Azidopyrrolidin-1-yl)-3-[(2-chlorophenyl)methyl]-5-[difluoro(phenyl)methyl]-3H-[1,2,3]triazolo[4,5-d]pyrimidine

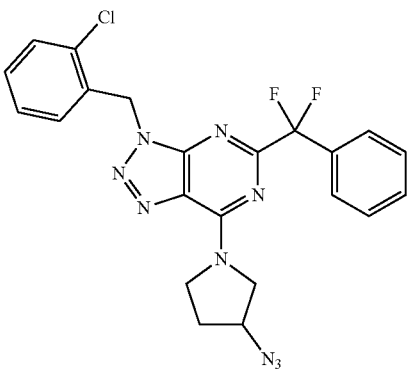 [SMILES: [N-]=[N+]=NC1CCN(c2nc(C(F)(F)c3ccccc3)nc3c2nnn3Cc2ccccc2Cl)C1]

In analogy to the procedure described for the synthesis of 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine (example 14) the title compound was prepared from 1-(3-(2-chlorobenzyl)-5-(difluoro(phenyl)methyl)-3H-[1,2,3]triazolo[4,5-d]pyrimidin-7-yl)pyrrolidin-3-yl methanesulfonate (64 mg, 0.12 mmol, 1.0 equiv) and isolated as a colorless solid (47 mg, 0.098 mmol, 82% yield). HRMS (ESI+) 482.1412 (M+H⁺).

Example 22

3-[(2-Chlorophenyl)methyl]-5-[difluoro(phenyl)methyl]-7-(3-isothiocyanatopyrrolidin-1-yl)-3H-[1,2,3]triazolo[4,5-d]pyrimidine

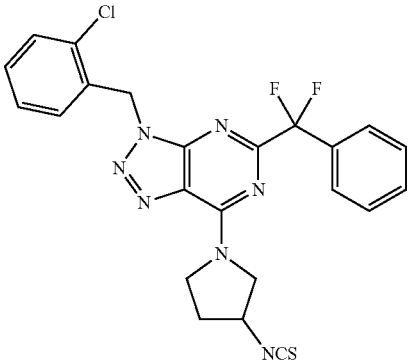

7-(3-Azidopyrrolidin-1-yl)-3-[(2-chlorophenyl)methyl]-5-[difluoro(phenyl)methyl]-3H-[1,2,3]triazolo[4,5-d]pyrimidine (31 mg, 0.064 mmol, 1.0 equiv) and CS₂ (39 μL, 0.64 mmol, 10 equiv) were dissolved in THF (322 μL) and PPh₃ (20 mg, 0.77 mmol, 1.2 equiv) was added. The reaction mix was stirred overnight at room temperature. Celite was added and the solvent was removed. Flash chromatography on silica (25% EtOAc in hexanes) afforded 3-[(2-chlorophenyl)methyl]-5-[difluoro(phenyl)methyl]-7-(3-isothiocyanatopyrrolidin-1-yl)-3H-[1,2,3]triazolo[4,5-d]pyrimidine (16 mg, 0.032 mmol, 50% yield) as colorless oil. HRMS (ESI+) 498.1069 (M+H⁺).

Example 23

5-[Difluoro(phenyl)methyl]-7-(3-isothiocyanatopyrrolidin-1-yl)-3-[(4-methyl-1,2,5-oxadiazol-3-yl)methyl]-3H-[1,2,3]triazolo[4,5-d]pyrimidine

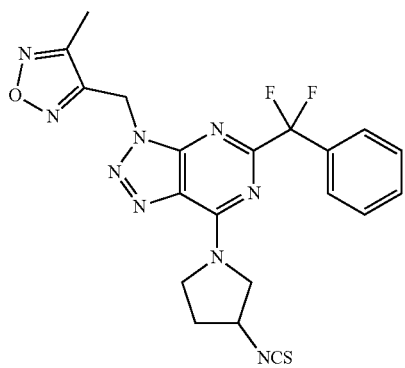

In analogy to the procedure described for the synthesis of 3-[(2-chlorophenyl)methyl]-5-[difluoro(phenyl)methyl]-7-(3-isothiocyanatopyrrolidin-1-yl)-3H-[1,2,3]triazolo[4,5-d]pyrimidine (example 22), the title compound was prepared from 7-(3-azidopyrrolidin-1-yl)-5-[difluoro(phenyl)methyl]-3-[(4-methyl-1,2,5-oxadiazol-3-yl)methyl]-3H-[1,2,3]triazolo[4,5-d]pyrimidine (39 mg, 0.086 mmol, 1.0 equiv) and isolated as a colorless oil (18 mg, 0.038 mmol, 45% yield). HRMS (ESI+) 470.1314 (M+H$^+$).

Example 24

2-[[5-[Difluoro(phenyl)methyl]-7-[(3S)-3-hydroxypyrrolidin-1-yl]triazolo[4,5-d]pyrimidin-3-yl]methyl]benzenesulfonyl fluoride

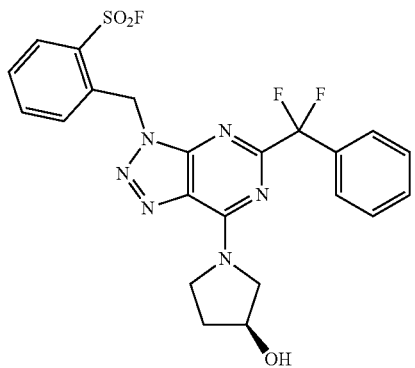 [SMILES: O=S(=O)(F)c1ccccc1Cn1nnc2c(N3CC[C@H](O)C3)nc(C(F)(F)c3ccccc3)nc21]

a) 5-Amino-1-(2-(benzylthio)benzyl)-1H-1,2,3-triazole-4-carboxamide

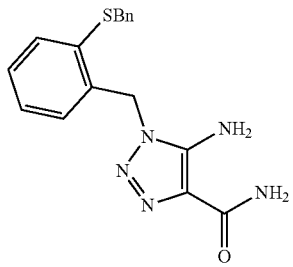

In analogy to the procedure described for the 5-amino-1-(2-vinylbenzyl)-1H-1,2,3-triazole-4-carboxamide (example 27, step a), the title compound was prepared from o-benzylmercaptobenzyl chloride (CAS 4521-46-4, 3.39 g, 13.6 mmol, 1.00 equiv), sodium azide (930 mg, 14.3 mmol, 1.05 equiv) and 2-cyanoacetamide (1.72 g, 20.4 mmol, 1.50 equiv) and isolated as colorless solid (4.03 g, 11.9 mmol, 87%). HRMS (ESI+) 362.1051 (M+Na$^+$).

b) 3-(2-(Benzylthio)benzyl)-5-(difluoro(phenyl)methyl)-3H-[1,2,3]triazolo[4,5-d]pyrimidin-7(4H)-one

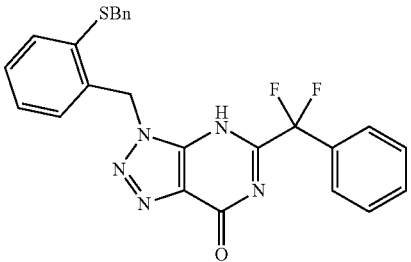

5-Amino-1-(2-(benzylthio)benzyl)-1H-1,2,3-triazole-4-carboxamide (679 mg, 2.00 mmol, 1.00 equiv) was combined with DMF (4 mL), 2,2-difluoro-2-phenylacetonitrile (459 mg, 3.00 mmol, 1.50 equiv) and K$_2$CO$_3$ (1.38 g, 10.0 mmol, 5.00 equiv) and heated to 90° C. overnight. After cooling to rt, water was added. The precipitate was filtered to yield impure material. Further purification by flash chromatography on silica (20% acetone in toluene) afforded the title compound as yellow solid (406 mg, 0.854 mmol, 43%). HRMS (ESI+) 479.1347 (M+H$^+$).

c) 2-((7-Chloro-5-(difluoro(phenyl)methyl)-3H-[1,2,3]triazolo[4,5-d]pyrimidin-3-yl)methyl)benzene-1-sulfonyl fluoride

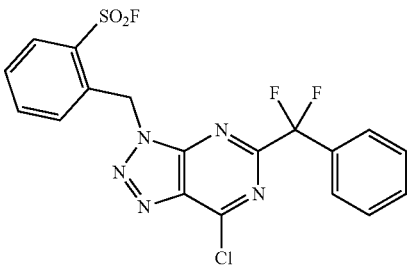 [SMILES: O=S(=O)(F)c1ccccc1Cn1nnc2c(Cl)nc(C(F)(F)c3ccccc3)nc21]

3-(2-(Benzylthio)benzyl)-5-(difluoro(phenyl)methyl)-3H-[1,2,3]triazolo[4,5-d]pyrimidin-7(4H)-one (150 mg, 0.315 mmol, 1.00 equiv) was combined with MeCN (6.4 mL), AcOH (80 µL) and water (0.16 mL) and cooled to −13° C. (icewater NaCl, external temperature). 1,3-Dichloro-5,5-dimethylhydantoin (124 mg, 0.631 mmol, 2.00 equiv) was added and it was stirred at the same temperature for 1.5 h. The reaction mixture was then diluted with CH$_2$Cl$_2$ (100 mL), washed with brine, dried over MgSO$_4$, filtered and concentrated. The crude material was dissolved in a mixture of acetone (1.0 mL) and water (50 µL). Potassium fluoride (92 mg, 1.6 mmol, 5.0 equiv) was added at rt and it was stirred overnight. The reaction mixture was diluted with CH$_2$Cl$_2$ (100 mL), filtered, dried over MgSO$_4$, filtered again and concentrated. The residue was redissolved in CH$_2$Cl$_2$ (1.6 mL). DMF (25 µL, 0.32 mmol, 1.0 equiv) was added followed by oxalyl chloride (56 µL, 0.63 mmol, 2.0 equiv). The reaction mixture was heated at reflux overnight. As TLC analysis indicated incomplete conversion, another portion of oxalyl chloride (56 µL, 0.63 mmol, 2.0 equiv) was added and stirring continued at reflux temperature for 2 h. The reaction

41 mixture was cooled to rt, diluted with EtOAc (100 mL), washed with halfsaturated aq. sodium bicarbonate, 5% aq. LiCl and brine, dried over MgSO$_4$, filtered and concentrated. Flash chromatography on silica (10% EtOAc in hexanes to 15% to 20%) afforded the title compound as yellow oil (48 mg, 0.11 mmol, 33% over 3 steps). HRMS (ESI+) 454.0352 (M+H$^+$).

d) 2-[[5-[Difluoro(phenyl)methyl]-7-[(3S)-3-hydroxypyrrolidin-1-yl]triazolo[4,5-d]pyrimidin-3-yl]methyl]benzenesulfonyl fluoride

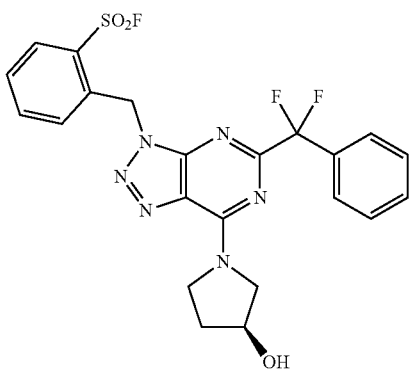 [SMILES: O=S(=O)(F)c1ccccc1Cn1nnc2c(N3CC[C@H](O)C3)nc(C(F)(F)c3ccccc3)nc21]

2-((7-Chloro-5-(difluoro(phenyl)methyl)-3H-[1,2,3]triazolo[4,5-d]pyrimidin-3-yl)methyl)benzene-1-sulfonyl fluoride (20 mg, 0.044 mmol, 1.0 equiv) was combined with (S)-pyrrolidin-3-ol (4.2 mg, 0.048 mmol, 1.1 equiv) and CH$_2$Cl$_2$ (0.2 mL). Triethylamine (9.2 µL, 0.066 mmol, 1.5 equiv) was added. After 30 min at rt, the reaction mixture was diluted with EtOAc (50 mL), washed with 5% aq. LiCl, and brine (2×), dried over MgSO$_4$, filtered and concentrated. Flash chromatography on silica (50% EtOAc in hexanes) afforded the title compound as colorless oil (16 mg, 0.032 mmol, 72%). HRMS (ESI+) 505.1261 (M+H$^+$).

Example 25

2-[[2-[[5-tert-Butyl-7-(3,3-difluoropyrrolidin-1-yl)triazolo[4,5-d]pyrimidin-3-yl]methyl]phenyl]methyldisulfanyl]ethanol

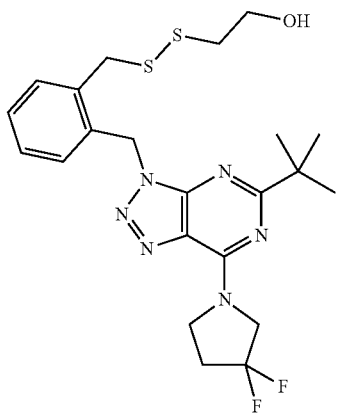 [SMILES: CC(C)(C)c1nc(N2CCC(F)(F)C2)c2nnn(Cc3ccccc3CSSCCO)c2n1]

a) S-2-((5-(tert-Butyl)-7-(3,3-difluoropyrrolidin-1-yl)-3H-[1,2,3]triazolo[4,5-d]pyrimidin-3-yl)methyl)benzyl benzothioate

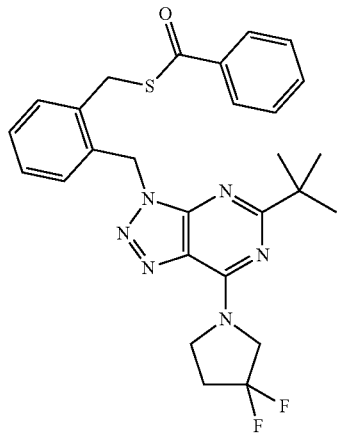 [SMILES: CC(C)(C)c1nc(N2CCC(F)(F)C2)c2nnn(Cc3ccccc3CSC(=O)c3ccccc3)c2n1]

S-2-(Iodomethyl)benzyl benzothioate (160 mg, 0.435 mmol, 1.05 equiv) and 5-tert-butyl-7-(3,3-difluoropyrrolidin-1-yl)-3H-[1,2,3]triazolo[4,5-d]pyrimidine (CAS 1438465-59-8, 117 mg, 0.414 mmol, 1.00 equiv) were dissolved in DMF (0.8 mL). NEt$_3$ (87 µL, 0.62 mmol, 1.5 equiv) was added and it was stirred at rt overnight. The reaction mixture was diluted with EtOAc (80 mL), washed with 5% aq. LiCl (3×10 mL), brine (10 mL), dried over MgSO$_4$, filtered and concentrated. Flash chromatography on silica (5% EtOAc in hexanes to 20%) afforded the title compound as colorless oil (90 mg, 0.172 mmol, 42%). HRMS (ESI+) 523.2083 (M+H$^+$).

b) 2-[[2-[[5-tert-Butyl-7-(3,3-difluoropyrrolidin-1-yl)triazolo[4,5-d]pyrimidin-3-yl]methyl]phenyl]methyldisulfanyl]ethanol S-2-((5-(tert-Butyl)-7-(3,3-difluoropyrrolidin-1-yl)-3H-[1,2,3]triazolo[4,5-d]pyrimidin-3-yl)methyl)benzyl benzothioate (34 mg, 0.065 mmol, 1.0 equiv) was dissolved in a mixture of MeOH (1 mL) and THF (0.8 mL). K$_2$CO$_3$ (45 mg, 0.33 mmol, 5.0 equiv) was added and it was stirred until TLC indicated full conversion of starting material. The mixture was then diluted with EtOAc (50 mL), washed with aq. HCl (0.5 M), water and brine (10 mL each), dried over MgSO$_4$, filtered and concentrated. The residue was dissolved in CH$_2$Cl$_2$ (0.2 mL) and added to a solution of benzotriazole (7.7 mg, 0.065 mmol, 1.0 equiv) and 1-chlorobenzotriazole (15 mg, 0.095 mmol, 1.5 equiv) in CH$_2$Cl$_2$ (0.65 mL) at −78° C. The solution was warmed to −20° C. and kept at that temperature for 20 min. A solution of mercaptoethanol in CH$_2$Cl$_2$ (0.5 M, 0.21 mL, 0.11 mmol, 1.6 equiv) was added. The solution was kept at −20° C. for 30 min. The reaction was quenched by the addition of a solution of sodium thiosulfate-5H$_2$O (16 mg, 0.065 mmol, 1.0 equiv) in water (0.4 mL) and sat. sodium bicarbonate (0.4 mL) and it was stirred at 0° C. for 10 min. Water (5 mL) was added and the aqueous phase was extracted with CH$_2$Cl$_2$ (3×2 mL). The combined organics were dried over MgSO$_4$, filtered and concentrated. Flash chromatography on silica (5% EtOAc in hexanes to 25%) afforded product contaminated with benzotriazole. A second flash chromatography on silica (7.5%

EtOAc in CH$_2$Cl$_2$) afforded the title compound as colorless oil (7.0 mg, 0.014 mmol, 22% over two steps). HRMS (ESI+) 495.1808 (M+H$^+$).

Example 26

2-[[5-[Difluoro(phenyl)methyl]-7-(3,3-difluoropyrrolidin-1-yl)triazolo[4,5-d]pyrimidin-3-yl]methyl]benzenesulfonyl fluoride

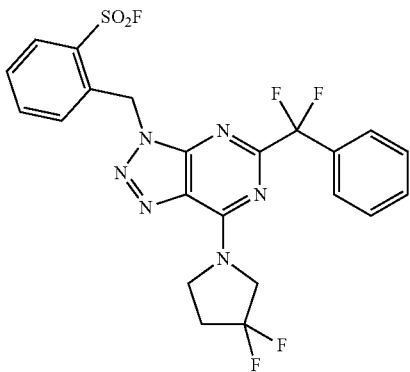 [SMILES: O=S(=O)(F)c1ccccc1Cn1nnc2c(N3CCC(F)(F)C3)nc(C(F)(F)c3ccccc3)nc21]

2-((7-Chloro-5-(difluoro(phenyl)methyl)-3H-[1,2,3]triazolo[4,5-d]pyrimidin-3-yl)methyl)benzene-1-sulfonyl fluoride (10 mg, 0.022 mmol, 1.0 equiv) and 3,3-difluoropyrrolidine hydrochloride (3.3 mg, 0.023 mmol, 1.05 equiv) were combined with CH$_2$Cl$_2$ (0.1 mL). Triethylamine (7 μL, 0.46 mmol, 2.1 equiv) was added. After 30 min, the mixture was directly subjected to flash chromatography to yield the title compound as colorless foam (10 mg, 0.019 mmol, 87%).

Example 27

5-[Difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine

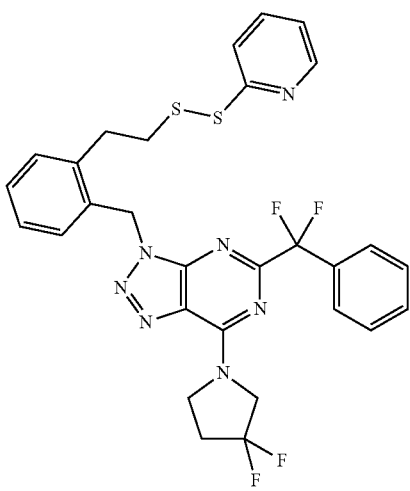 [SMILES: FC1(F)CCN(c2nc(C(F)(F)c3ccccc3)nc3c2nnn3Cc2ccccc2CCSSc2ccccn2)C1]

a) 5-Amino-1-(2-vinylbenzyl)-1H-1,2,3-triazole-4-carboxamide

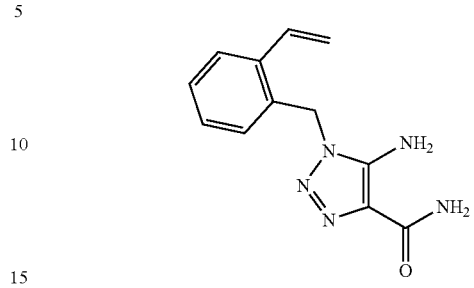

Sodium azide (0.852 g, 13.1 mmol, 1.05 eq.) was added in portions to a solution of chloromethylstyrene (CAS 22570-84-9, 1.91 g, 12.5 mmol, 1.00 equiv) and DIPEA (0.22 mL, 1.3 mmol, 0.10 equiv) in DMSO (12.5 mL) and stirred for 1.5 h at rt. The suspension then was transferred to a solution of 2-cyanoacetamide (1.58 g, 18.7 mmol, 1.50 equiv) and 20% aq. NaOH (2.25 mL, 12.5 mmol, 1.00 equiv) in DMSO (12.5 mL) and the resulting mixture was stirred for 3.5 h at rt. Water (100 mL) was added while cooling with an icebath. After 20 min, the suspension was filtered. The filtercake was washed with water (3×40 mL), EtOH (2×20 mL) and diethylether (2×20 mL) to yield the title compound as colorless solid (2.23 g, 9.15 mmol, 73%). $^1$H NMR (300 MHz, Acetone-d6) δ 7.63-7.56 (m, 1H), 7.38-7.23 (m, 2H), 7.17 (dd, J=17.3, 11.0 Hz, 1H), 7.02 (s, 1H), 6.90-6.81 (m, 1H), 6.41 (s, 1H), 5.97 (s, 2H), 5.75 (dd, J=17.3, 1.4 Hz, 1H), 5.54 (s, 2H), 5.38 (dd, J=11.1, 1.3 Hz, 1H).

b) 5-(Difluoro(phenyl)methyl)-3-(2-vinylbenzyl)-3H-[1,2,3]triazolo[4,5-d]pyrimidin-7(4H)-one

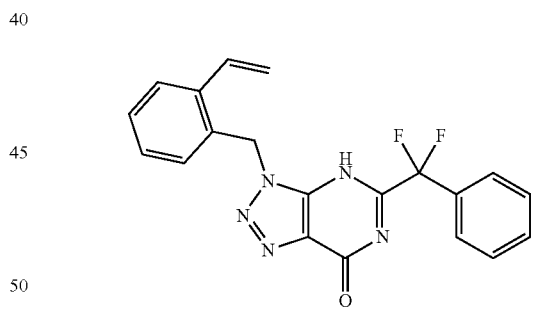

2,2-Difluoro-2-phenylacetonitrile (629 mg, 4.11 mmol, 2.00 equiv) and K$_2$CO$_3$ (1.42 g, 10.3 mmol, 5.00 equiv) were added to a solution of 5-amino-1-(2-vinylbenzyl)-1H-1,2,3-triazole-4-carboxamide (500 mg, 2.06 mmol, 1.00 equiv) in DMF (6.9 mL). The flask was capped and placed in an oilbath preheated to 80° C. After 3 h, additional 2,2-difluoro-2-phenylacetonitrile (157 mg, 1.03 mmol, 0.50 equiv) was added and the mixture was stirred overnight at 80° C. After cooling to rt, water (10 mL) and 2 M aq. HCl (5.2 mL) were added. The resulting suspension was stirred for 20 min and then filtered. The filtercake was washed with water (30 mL), EtOH (30 mL) and ether (30 mL), and dried to afford the title compound as colorless solid (357 mg, 0.941 mmol, 46%). HRMS (ESI+) 380.1319 (M+H$^+$).

c) 7-Chloro-5-(difluoro(phenyl)methyl)-3-(2-vinyl-benzyl)-3H-[1,2,3]triazolo[4,5-d]pyrimidine

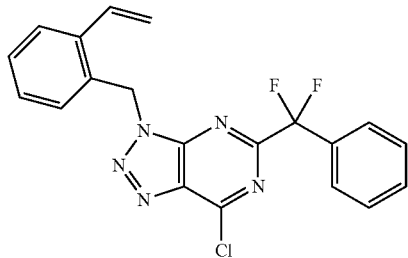 [SMILES: C=Cc1ccccc1Cn1nnc2c(Cl)nc(C(F)(F)c3ccccc3)nc21]

POCl$_3$ (0.36 mL, 3.9 mmol, 2.0 equiv) was added to a solution of 5-(difluoro(phenyl)methyl)-3-(2-vinylbenzyl)-3H-[1,2,3]triazolo[4,5-d]pyrimidin-7(4H)-one (0.74 g, 2.0 mmol, 1.0 equiv) and DMF (cat.) in a mixture of toluene (14.8 mL) and MeCN (14.8 mL). The resulting mixture was stirred for at 80° C. for 6 h. Additional POCl$_3$ (0.37 mL, 4.0 mmol, 1.0 equiv) was added and the mixture was stirred overnight at 80° C. After cooling to rt, EtOAc (80 mL) was added. The solution was washed with water (30 mL) and brine (30 mL). The organics were dried over MgSO$_4$ and filtered and concentrated. Flash chromatography on silica (10% EtOAc in hexanes) afforded the title compound (617 mg, 1.55 mmol, 80%) as yellow solid. HRMS (ESI+) 398.0986 (M+H$^+$).

d) 5-(Difluoro(phenyl)methyl)-7-(3,3-difluoropyrro-lidin-1-yl)-3-(2-vinylbenzyl)-3H-[1,2,3]triazolo[4,5-d]pyrimidine

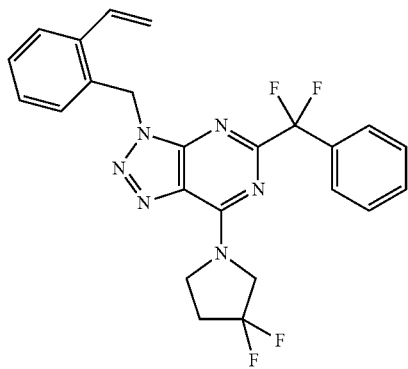 [SMILES: C=Cc1ccccc1Cn1nnc2c(N3CCC(F)(F)C3)nc(C(F)(F)c3ccccc3)nc21]

Triethylamine (70 µL, 0.50 mmol, 2.5 equiv) was added to a mixture of 7-chloro-5-(difluoro(phenyl)methyl)-3-(2-vinylbenzyl)-3H-[1,2,3]triazolo[4,5-d]pyrimidine (80 mg, 0.20 mmol, 1.0 equiv) and 3,3-difluoropyrrolidine hydrochloride (35 mg, 0.24 mmol, 1.2 equiv) in CH$_2$Cl$_2$ (2 mL). The resulting mixture was stirred overnight at rt. The volatiles were removed and the residue subjected to flash chromatography on silica (10% EtOAc in hexanes) to afford the title compound (91 mg, 0.19 mmol, 97%) as colorless oil. HRMS (ESI+) 469.1758 (M+H$^+$).

e) S-2-((5-(Difluoro(phenyl)methyl)-7-(3,3-difluoro-pyrrolidin-1-yl)-3H-[1,2,3]triazolo[4,5-d]pyrimidin-3-yl)methyl)phenethyl ethanethioate

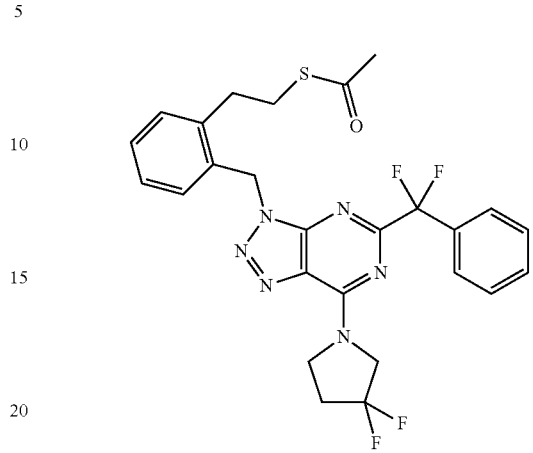

5-(Difluoro(phenyl)methyl)-7-(3,3-difluoropyrrolidin-1-yl)-3-(2-vinylbenzyl)-3H-[1,2,3]triazolo[4,5-d]pyrimidine (20 mg, 0.043 mmol, 1.0 equiv) was combined with DMF (0.7 mL), thioacetic acid (0.012 mL, 0.17 mmol, 4.0 equiv) and Bi$_2$O$_3$ (0.2 mg, 0.4 µmol, 0.01 equiv) and the mixture was sparged with nitrogen. BrCCl$_3$ (0.4 µL, 4 µmol, 0.1 equiv) was added and the mixture was irradiated with a household bulb (15 W) overnight. After the addition of EtOAc and water, the layers were separated. The organic layer was washed with 5% aq. LiCl and brine. The organics were dried over MgSO$_4$, filtered and concentrated. Flash chromatography on silica (10-40% EtOAc in hexanes) afforded the title compound (10 mg, 0.018 mmol, 43%). HRMS (ESI+) 567.1549 (M+Na$^+$).

f) 2-(2-((5-(Difluoro(phenyl)methyl)-7-(3,3-difluo-ropyrrolidin-1-yl)-3H-[1,2,3]triazolo[4,5-d]pyrimi-din-3-yl)methyl)phenyl)ethanethiol

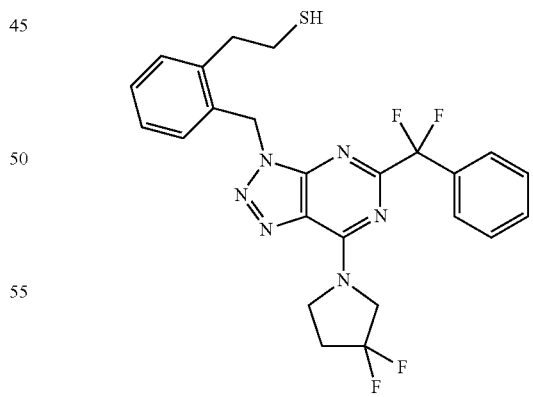

K$_2$CO$_3$ (37 mg, 0.26 mmol, 2.0 equiv) was added to a solution of S-2-((5-(Difluoro(phenyl)methyl)-7-(3,3-difluo-ropyrrolidin-1-yl)-3H-[1,2,3]triazolo[4,5-d]pyrimidin-3-yl) methyl)phenethyl ethanethioate (72 mg, 0.13 mmol, 1.0 equiv) in a mixture of MeOH (1.0 mL) and THF (0.2 mL). The resulting reaction mixture was stirred for 24 h. EtOAc (30 mL) was added. The organics were washed with 2 M aq.

HCl (20 mL), water (20 mL) and brine (20 mL). After drying over MgSO₄ and filtration, the solvent was removed to afford the title compound (64 mg, 0.13 mmol, 96%) which was used as such for subsequent reactions.

g) 5-[Difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine 2-(2-((5-(Difluoro(phenyl)methyl)-7-(3,3-difluoropyrrolidin-1-yl)-3H-[1,2,3]triazolo[4,5-d]pyrimidin-3-yl)methyl)phenyl)ethanethiol (20 mg, 0.040 mmol, 1.0 equiv) was added to a solution of 1-chlorobenzotriazole (9.2 mg, 0.060 mmol, 1.5 equiv) and benzotriazole (4.7 mg, 0.040 mmol, 1.0 equiv) in CH₂Cl₂ (0.4 mL) at −78° C. and stirred for 1 h at −20° C. Pyridine-2-thiol (6.6 mg, 0.060 mmol, 1.5 equiv) was added at −20° C. and the mixture was stirred for 6 h. The mixture was quenched with aqueous Na₂S₂O₃ and sat. aqueous NaHCO₃. The organic layer was separated and the aqueous phase extracted with CH₂Cl₂ (3×10 mL). The combined organics were concentrated and the residue subjected to preparative TLC (20% EtOAc in hexanes) to afford the title compound (6.5 mg, 0.001 mmol, 27%) as a colorless oil. HRMS (ESI+) 612.1613 (M+H⁺).

Example 28

2-[2-[2-[[5-[Difluoro(phenyl)methyl]-7-(3,3-difluoropyrrolidin-1-yl)triazolo[4,5-d]pyrimidin-3-yl]methyl]phenyl]ethyldisulfanyl]ethanol

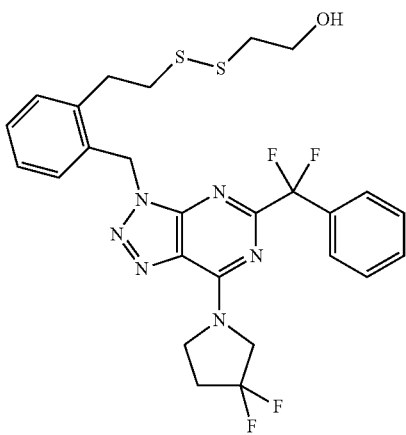 [SMILES: OCCSSCCc1ccccc1Cn1nnc2c(N3CCC(F)(F)C3)nc(C(F)(F)c3ccccc3)nc21]

Iodine (30 mg, 0.12 mmol, 3.0 equiv) was added in portions to a solution of 2-mercaptoethanol (0.014 mL, 0.20 mmol, 5.0 equiv), pyridine (0.019 mL, 0.24 mmol, 6.0 equiv) and 2-(2-((5-(difluoro(phenyl)methyl)-7-(3,3-difluoropyrrolidin-1-yl)-3H-[1,2,3]triazolo[4,5-d]pyrimidin-3-yl)methyl)phenyl)ethanethiol (20 mg, 0.040 mmol, 1.0 equiv) in CH₂Cl₂ (0.3 mL) and MeOH (0.1 mL). The resulting mixture was stirred for 2 h at rt. EtOAc (20 mL) was added and the solution was washed with brine (10 mL). The organics were dried over MgSO₄, filtered and concentrated. Preparative TLC (5% EtOAc in CH₂Cl₂) afforded the title compound (9 mg, 0.02 mmol, 39%). HRMS (ESI+) 579.1613 (M+H⁺).

Example 29

2-[2-[2-[[5-tert-Butyl-7-(3,3-difluoropyrrolidin-1-yl)triazolo[4,5-d]pyrimidin-3-yl]methyl]phenyl]ethyldisulfanyl]ethanol

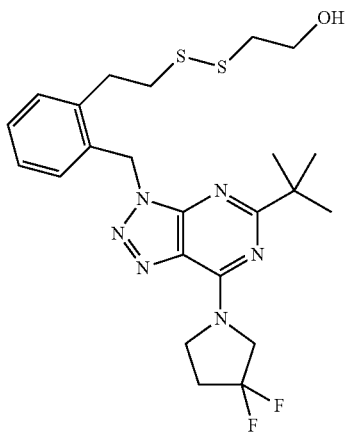 [SMILES: CC(C)(C)c1nc(N2CCC(F)(F)C2)c2nnn(Cc3ccccc3CCSSCCO)c2n1]

a) 5-(tert-Butyl)-7-chloro-3-(2-vinylbenzyl)-3H-[1,2,3]triazolo[4,5-d]pyrimidine

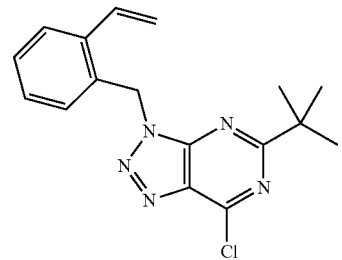 [SMILES: C=Cc1ccccc1Cn1nnc2c(Cl)nc(C(C)(C)C)nc21]

5-Amino-1-(2-vinylbenzyl)-1H-1,2,3-triazole-4-carboxamide (1.00 g, 4.11 mmol, 1.00 equiv) was dissolved in dimethylacetamide (3.4 mL). Pyridine (0.499 mL, 6.17 mmol, 1.50 equiv) and pivaloyl chloride (0.759 mL, 6.17 mmol, 1.50 equiv) were added. The resulting mixture was stirred at 85° C. for 5.5 h, before KHCO₃ (2.06 g, 20.6 mmol, 5.00 equiv) was added. The temperature was increased to 155° C. and it was stirred overnight. The reaction mix was cooled to rt. Water was added and the resulting suspension was filtered. The filtercake was washed with ethanol and ether, and dried to afford intermediate triazolopyrimidone (1.22 g). The intermediate was combined with MeCN (11.4 mL), POCl₃ (0.74 mL, 7.9 mmol, 2.0 equiv) and N,N-diethylaniline (0.63 mL, 4.0 mmol, 1.0 equiv). The resulting mixture was stirred at 80° C. overnight. After cooling to rt, EtOAc (80 mL) was added. The solution was washed with water (30 mL) and brine (30 mL), dried over MgSO₄, filtered and concentrated. Flash chromatography on silica (10% EtOAc in hexanes) afforded the title compound as yellow solid (847 mg, 2.58 mmol, 63% over two steps). HRMS (ESI+) 328.1327 (M+H⁺).

b) 5-(tert-Butyl)-7-(3,3-difluoropyrrolidin-1-yl)-3-(2-vinylbenzyl)-3H-[1,2,3]triazolo[4,5-d]pyrimidine

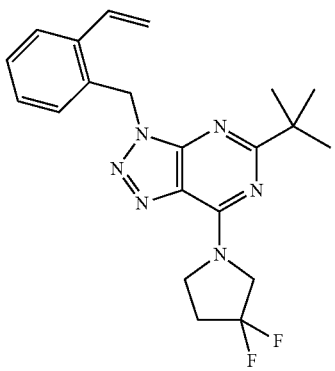 [SMILES: C=Cc1ccccc1Cn1nnc2c(N3CCC(F)(F)C3)nc(C(C)(C)C)nc21]

5-(tert-Butyl)-7-chloro-3-(2-vinylbenzyl)-3H-[1,2,3]triazolo[4,5-d]pyrimidine (847 mg, 2.58 mmol, 1.00 equiv) and 3,3-difluoropyrrolidine hydrochloride (445 mg, 3.10 mmol, 1.20 equiv) were combined with CH$_2$Cl$_2$ (25 mL). Triethylamine (0.90 mL, 6.5 mmol, 2.5 equiv) was added and the resulting mixture was stirred overnight at rt. The volatiles were removed and the residue subjected to flash chromatography on silica (10% EtOAc in hexanes) to afford the title compound as colorless oil (968 mg, 2.43 mmol, 94%). HRMS (ESI+) 399.2101 (ESI+H$^+$).

c) S-2-((5-(tert-Butyl)-7-(3,3-difluoropyrrolidin-1-yl)-3H-[1,2,3]triazolo[4,5-d]pyrimidin-3-yl)methyl)phenethyl ethanethioate

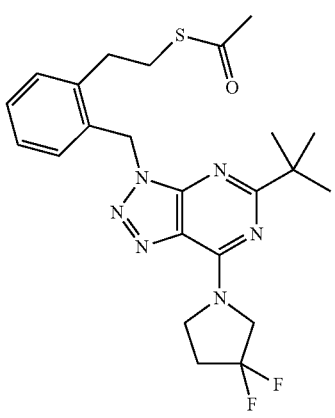 [SMILES: CC(=O)SCCc1ccccc1Cn1nnc2c(N3CCC(F)(F)C3)nc(C(C)(C)C)nc21]

AIBN (21 mg, 0.13 mmol, 0.10 equiv) was added to a solution of 5-(tert-butyl)-7-(3,3-difluoropyrrolidin-1-yl)-3-(2-vinylbenzyl)-3H-[1,2,3]triazolo[4,5-d]pyrimidine (500 mg, 1.26 mmol, 1.0 equiv) and thioacetic acid (0.90 mL, 13 mmol, 10 equiv) in toluene (5 mL). The mixture was purged with nitrogen for 10 min and heated at reflux temperature overnight. Additional AIBN (21 mg, 0.13 mmol, 0.10 equiv) was added and the mixture was refluxed for further 10 h. After cooling to rt, EtOAc (100 mL) was added. The solution was washed with saturated aq. sodium bicarbonate (2×40 mL) and brine (40 mL). The organics were dried over MgSO$_4$, filtered and concentrated. Flash chromatography on silica (10% EtOAc in hexanes) afforded the title compound (393 mg, 0.828 mmol, 66%).

d) 2-(2-((5-(tert-Butyl)-7-(3,3-difluoropyrrolidin-1-yl)-3H-[1,2,3]triazolo[4,5-d]pyrimidin-3-yl)methyl)phenyl)ethanethiol

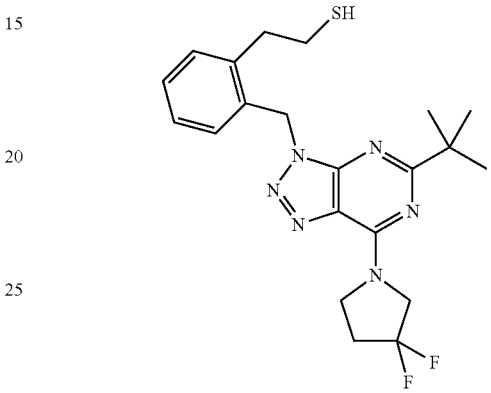

S-2-((5-(tert-Butyl)-7-(3,3-difluoropyrrolidin-1-yl)-3H-[1,2,3]triazolo[4,5-d]pyrimidin-3-yl)methyl)phenethyl ethanethioate (100 mg, 0.211 mmol, 1.00 equiv) was dissolved in MeOH (4.0 mL) and THF (1.0 mL). K$_2$CO$_3$ (58 mg, 0.42 mmol, 2.0 equiv) was added and the mixture was stirred overnight. EtOAc (40 mL) was added and the solution was washed with 2 M aq. HCl (20 mL), water (20 mL) and brine (20 mL). The organics were dried over MgSO$_4$, filtered and concentrated. The crude thiol was used in subsequent reactions without further purification.

e) 2-[2-[2-[[5-tert-Butyl-7-(3,3-difluoropyrrolidin-1-yl)triazolo[4,5-d]pyrimidin-3-yl]methyl]phenyl]ethyldisulfanyl]ethanol Iodine (35 mg, 0.14 mmol, 3.0 equiv) was added in portions to a solution of 2-mercaptoethanol (0.016 mL, 0.23 mmol, 5.0 equiv), pyridine (0.022 mL, 0.28 mmol, 6.0 equiv) and 2-(2-((5-(tert-butyl)-7-(3,3-difluoropyrrolidin-1-yl)-3H-[1,2,3]triazolo[4,5-d]pyrimidin-3-yl)methyl)phenyl)ethanethiol (20 mg, 0.046 mmol, 1.0 equiv) in CH$_2$Cl$_2$ (0.3 mL) and MeOH (0.1 mL). The resulting mixture was stirred for 8 h at rt. EtOAc (20 mL) was added and the solution was washed with brine (10 mL). The organics were dried over MgSO$_4$, filtered and concentrated. Preparative TLC (5% EtOAc in CH$_2$Cl$_2$) afforded the title compound (4 mg, 0.008 mmol, 17%). HRMS (ESI+) 509.1962 (M+H$^+$).

Example 30

3-[[2-[2-(Benzotriazol-1-ylsulfonyl)ethyl]phenyl]methyl]-5-tert-butyl-7-(3,3-difluoropyrrolidin-1-yl)triazolo[4,5-d]pyrimidine

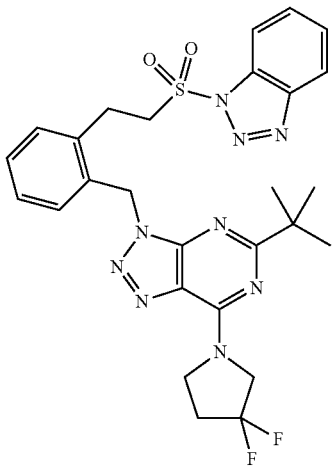 [SMILES: CC(C)(C)c1nc(N2CCC(F)(F)C2)c2nnn(Cc3ccccc3CCS(=O)(=O)n3nnc4ccccc43)c2n1]

2-(2-((5-(tert-Butyl)-7-(3,3-difluoropyrrolidin-1-yl)-3H-[1,2,3]triazolo[4,5-d]pyrimidin-3-yl)methyl)phenyl)ethanethiol (15 mg, 0.035 mmol, 1.0 eq.) was added to N-chlorobenzotriazole (8.0 mg, 0.052 mmol, 1.5 equiv) and benzotriazole (4.1 mg, 0.035 mmol, 1.0 equiv) in CH$_2$Cl$_2$ (0.3 mL) and stirred for 1 h at −78° C. Then 2-mercaptoethanol (7 µL, 0.1 mmol, 1.5 equiv) was added at −20° C. and the mixture was warmed to rt. The reaction was quenched by the addition of aqueous Na$_2$S$_2$O$_3$ and sat. aqueous NaHCO$_3$. The phases were separated and the aqueous phase was extracted with CH$_2$Cl$_2$ (3×10 mL). The combined organic layers were concentrated in vacuo and the residue was subjected to preparative TLC (20% EtOAc in hexanes) to yield the title compound (2 mg, 3 µmol, 10%). HRMS (ESI+) 582.2206 (M+H$^+$).

Example 31

2-[2-[[5-tert-Butyl-7-(3,3-difluoropyrrolidin-1-yl)triazolo[4,5-d]pyrimidin-3-yl]methyl]phenyl]ethanesulfonyl fluoride

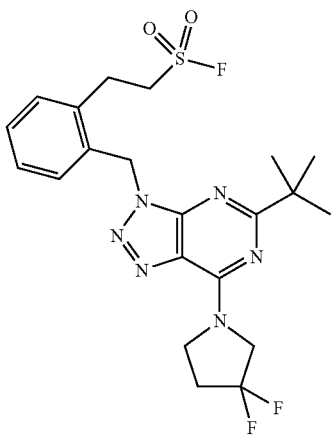 [SMILES: CC(C)(C)c1nc(N2CCC(F)(F)C2)c2nnn(Cc3ccccc3CCS(=O)(=O)F)c2n1]

N-chlorosuccinimide (20 mg, 0.15 mmol, 4.0 equiv) was slowly added to a solution of S-2-((5-(tert-Butyl)-7-(3,3-difluoropyrrolidin-1-yl)-3H-[1,2,3]triazolo[4,5-d]pyrimidin-3-yl)methyl)phenethyl ethanethioate (18 mg, 0.037 mmol, 1.0 equiv) in a mixture of MeCN (0.6 mL) and 2 M aq. HCl (0.12 mL, 0.24 mmol, 6.5 equiv) at 0° C. The resulting solution was stirred for 40 min. EtOAc (20 mL) and sat. NaHCO$_3$ (20 mL) were added and the layers were separated. The organic phase was washed with brine (20 mL), dried over MgSO$_4$ filtered and concentrated to give crude sulfonyl chloride, which was dissolved in a mixture of acetone (0.5 mL) and water (0.025 mL). Potassium fluoride (10 mg, 0.18 mmol, 5.0 equiv) was added and the mixture was stirred for 6.5 h at rt. EtOAc (20 mL) was added. The organics were washed with water (10 mL) and brine (10 mL), dried over MgSO$_4$, filtered and concentrated. Preparative TLC (20% EtOAc in hexanes) afforded the title compound (9 mg, 0.02 mmol, 53%). HRMS (ESI+) 483.1780 (M+H$^+$).

Example 32

5-tert-Butyl-7-(3,3-difluoropyrrolidin-1-yl)-3-[[2-[2-(pyridin-2-yldisulfanyl)ethyl]phenyl]methyl]triazolo[4,5-d]pyrimidine

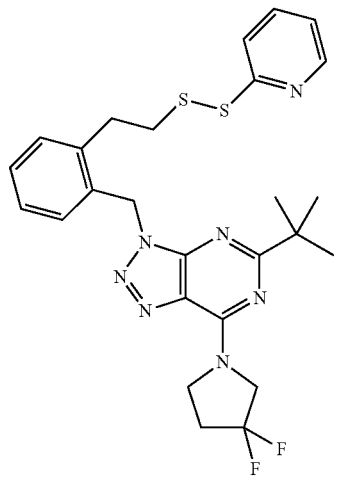 [SMILES: CC(C)(C)c1nc(N2CCC(F)(F)C2)c2nnn(Cc3ccccc3CCSSc3ccccn3)c2n1]

In analogy to the procedure described for the synthesis of 5-[difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine (example 27, step g) the title compound was prepared from 2-(2-((5-(tert-butyl)-7-(3,3-difluoropyrrolidin-1-yl)-3H-[1,2,3]triazolo[4,5-d]pyrimidin-3-yl)methyl)phenyl)ethanethiol (20 mg, 0.046 mmol, 1.0 equiv), pyridine-2-thiol (26 mg, 0.23 mmol, 5.0 equiv), iodine (35 mg, 0.14 mmol, 3.0 equiv) and pyridine (0.022 mL, 0.28 mmol, 6.0 equiv) in CH$_2$Cl$_2$ (0.3 mL) and isolated by preparative TLC (6 mg, 0.01 mmol, 24%). HRMS (ESI+) 542.1972 (M+H$^+$).

Example 33

2-[2-[2-[[5-tert-Butyl-7-(3,3-difluoropyrrolidin-1-yl)triazolo[4,5-d]pyrimidin-3-yl]methyl]phenyl]ethyldisulfanyl]ethanamine

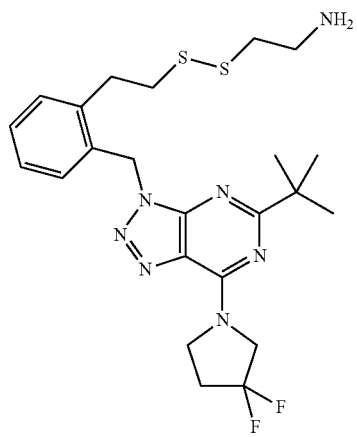 [SMILES: CC(C)(C)c1nc(N2CCC(F)(F)C2)c2nnn(Cc3ccccc3CCSSCCN)c2n1]

In analogy to the procedure described for the synthesis of 5-[difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine (example 27, step g) the title compound was prepared from 2-(2-((5-(tert-butyl)-7-(3,3-difluoropyrrolidin-1-yl)-3H-[1,2,3]triazolo[4,5-d]pyrimidin-3-yl)methyl)phenyl)ethanethiol (30 mg, 0.069 mmol, 1.0 equiv), 2-aminoethanethiol (27 mg, 0.35 mmol, 5.0 equiv), iodine (53 mg, 0.21 mmol, 3.0 equiv) and pyridine (0.034 mL, 0.42 mmol, 6.0 equiv) in CH$_2$Cl$_2$ (1.0 mL) and MeOH (0.3 mL) and isolated by preparative TLC (20% MeOH in CH$_2$Cl$_2$, 1% NEt$_3$) as an oil (5.5 mg, 0.008 mmol, 16%). HRMS (ESI+) 508.2118 (M+H$^+$).

Example 34

2-[2-[2-[[5-[Difluoro(phenyl)methyl]-7-(3,3-difluoropyrrolidin-1-yl)triazolo[4,5-d]pyrimidin-3-yl]methyl]phenyl]ethyldisulfanyl]ethanamine

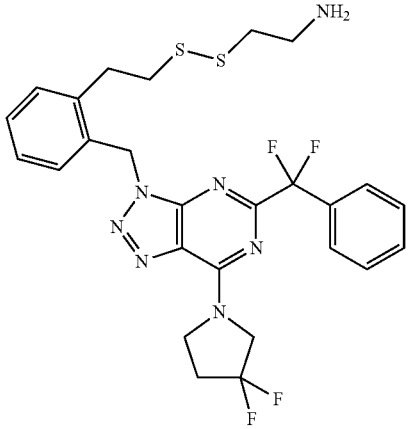 [SMILES: NCCSSCCc1ccccc1Cn1nnc2c(N3CCC(F)(F)C3)nc(C(F)(F)c3ccccc3)nc21]

In analogy to the procedure described for the synthesis of 5-[difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine (example 27, step g) the title compound was prepared from 2-(2-((5-(difluoro(phenyl)methyl)-7-(3,3-difluoropyrrolidin-1-yl)-3H-[1,2,3]triazolo[4,5-d]pyrimidin-3-yl)methyl)phenyl)ethanethiol (20 mg, 0.040 mmol, 1.0 equiv), 2-aminoethanethiol (15 mg, 0.20 mmol, 5.0 equiv), iodine (30 mg, 0.12 mmol, 3.0 equiv) and pyridine (0.019 mL, 0.24 mmol, 6.0 equiv) in CH$_2$Cl$_2$ (0.5 mL) and MeOH (0.2 mL) and isolated by preparative TLC (20% MeOH in CH$_2$Cl$_2$, 1% NEt$_3$) as an oil (4.5 mg, 0.008 mmol, 20%). HRMS (ESI+) 578.1774 (M+H$^+$).

Example 35

3-[2-[2-[[5-tert-Butyl-7-(3,3-difluoropyrrolidin-1-yl)triazolo[4,5-d]pyrimidin-3-yl]methyl]phenyl]ethyldisulfanyl]propane-1,2-diol

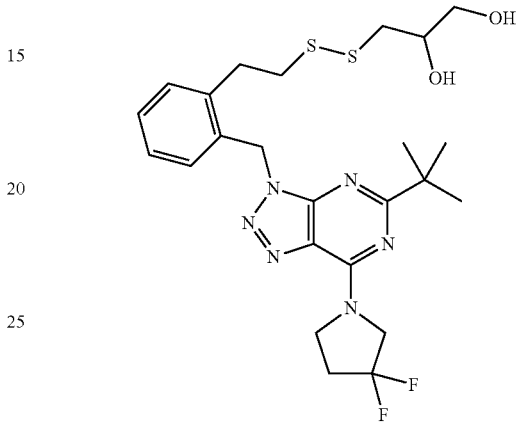

In analogy to the procedure described for the synthesis of 2-[[2-[[5-tert-butyl-7-(3,3-difluoropyrrolidin-1-yl)triazolo[4,5-d]pyrimidin-3-yl]methyl]phenyl]methyldisulfanyl]ethanol (example 25, step b) the title compound was prepared from S-2-((5-(tert-butyl)-7-(3,3-difluoropyrrolidin-1-yl)-3H-[1,2,3]triazolo[4,5-d]pyrimidin-3-yl)methyl)benzyl benzothioate (25 mg, 0.058 mmol, 1.0 equiv) and thioglycerol (9.4 mg, 0.087 mmol, 1.5 equiv) and isolated by preparative TLC (40% EtOAc in CH$_2$Cl$_2$) as colorless oil (22 mg, 0.041 mmol, 71%). HRMS (ESI+) 539.2070 (M+H$^+$).

Example 36

2-[[2-[[5-tert-Butyl-7-(3,3-difluoropyrrolidin-1-yl)triazolo[4,5-d]pyrimidin-3-yl]methyl]phenyl]disulfanyl]ethanol

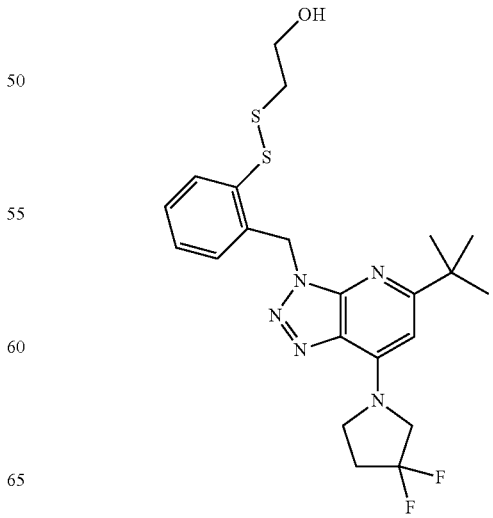

a) 5-Amino-1-(2-iodobenzyl)-1H-1,2,3-triazole-4-carboxamide

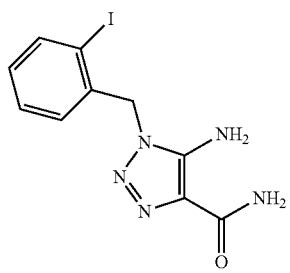 [SMILES: NC(=O)c1nnn(Cc2ccccc2I)c1N]

In analogy to the procedure described for the synthesis of 5-amino-1-(2-vinylbenzyl)-1H-1,2,3-triazole-4-carboxamide (example 27, step a) the title compound was prepared from 2-iodobenzyl methanesulfonate (CAS 183789-20-0, 6.67 g, 21.4 mmol, 1.00 equiv) and isolated as colorless solid (6.32 g, 18.4 mmol, 86%). HRMS (ESI+) 344.0010 (M+H$^+$).

b) 5-(tert-Butyl)-3-(2-iodobenzyl)-3H-[1,2,3]triazolo[4,5-b]pyridin-7(4H)-one

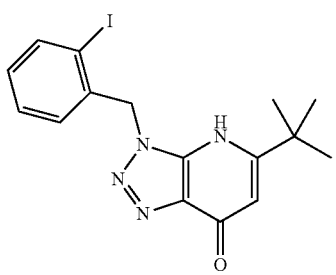 [SMILES: CC(C)(C)c1cc(=O)c2nnn(Cc3ccccc3I)c2[nH]1]

5-Amino-1-(2-iodobenzyl)-1H-1,2,3-triazole-4-carboxamide (0.500 g, 1.46 mmol, 1.00 equiv) was dissolved in dimethylacetamide (2.4 mL). Pyridine (0.18 mL, 2.2 mmol, 1.5 equiv) and pivaloyl chloride (0.27 mL, 2.2 mmol, 1.5 equiv) were added and the mixture was stirred at 85° C. for 4 h. KHCO$_3$ (1.01 g, 7.29 mmol, 5.0 equiv) was added and the mixture was stirred at 155° C. overnight. The solution was cooled to rt. Water (100 mL) was added and the resulting suspension was filtered. The filter cake was washed with water (50 mL), EtOH (50 mL) and diethylether (50 mL), and dried to afford the title compound (120 mg, 0.293 mmol, 20%) as colorless solid. HRMS (ESI+) 410.0467 (M+H$^+$).

c) 5-(tert-Butyl)-7-chloro-3-(2-iodobenzyl)-3H-[1,2,3]triazolo[4,5-b]pyridine

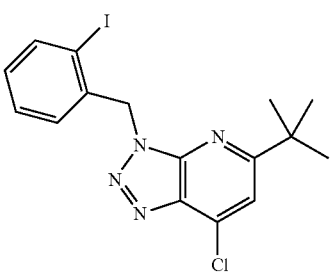 [SMILES: CC(C)(C)c1cc(Cl)c2nnn(Cc3ccccc3I)c2n1]

In analogy to the procedure described for the synthesis of 7-chloro-5-(difluoro(phenyl)methyl)-3-(2-vinylbenzyl)-3H-[1,2,3]triazolo[4,5-d]pyrimidine (example 27, step c), the title compound was prepared from 5-(tert-butyl)-3-(2-iodobenzyl)-3H-[1,2,3]triazolo[4,5-b]pyridin-7(4H)-one (180 mg, 0.440 mmol, 1.00 equiv) and isolated as colorless solid (130 mg, 0.304 mmol, 69%). HRMS (ESI+) 428.0128 (M+H$^+$).

d) 5-(tert-Butyl)-7-(3,3-difluoropyrrolidin-1-yl)-3-(2-iodobenzyl)-3H-[1,2,3]triazolo[4,5-b]pyridine

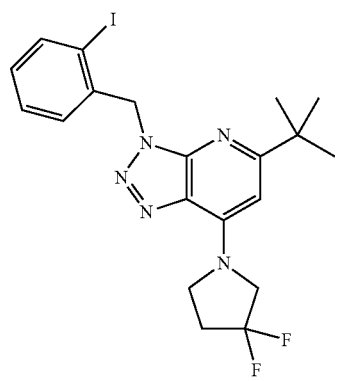 [SMILES: CC(C)(C)c1cc(N2CCC(F)(F)C2)c2nnn(Cc3ccccc3I)c2n1]

In analogy to the procedure described for the synthesis of 5-(difluoro(phenyl)methyl)-7-(3,3-difluoropyrrolidin-1-yl)-3-(2-vinylbenzyl)-3H-[1,2,3]triazolo[4,5-d]pyrimidine (example 27, step d) the title compound was prepared from 5-(tert-butyl)-7-chloro-3-(2-iodobenzyl)-3H-[1,2,3]triazolo[4,5-b]pyridine (128 mg, 0.299 mmol, 1.00 equiv) and isolated as colorless oil (148 mg, 0.299 mmol, 99%). HRMS (ESI+) 409.0908 (M+H$^+$).

e) S-(2-((5-(tert-Butyl)-7-(3,3-difluoropyrrolidin-1-yl)-3H-[1,2,3]triazolo[4,5-b]pyridin-3-yl)methyl)phenyl)ethanethioate

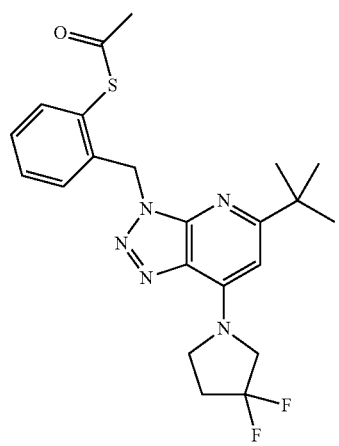 [SMILES: CC(=O)Sc1ccccc1Cn1nnc2c(N3CCC(F)(F)C3)cc(C(C)(C)C)nc21]

5-(tert-Butyl)-7-(3,3-difluoropyrrolidin-1-yl)-3-(2-iodobenzyl)-3H-[1,2,3]triazolo[4,5-b]pyridine (20 mg, 0.040 mmol, 1.0 equiv) was dissolved in toluene (0.4 mL) and purged with nitrogen. Copper iodide (0.8 mg, 4 μmol, 0.1 equiv), 1,10-phenanthroline (1.5 mg, 8.0 μmol, 0.2 equiv)

and potassium thioacetate (6.9 mg, 0.060 mmol, 1.5 equiv) were added and the mixture was stirred at 100° C. for 19 h. Water (20 mL) and EtOAc (20 mL) were added and the mixture was stirred for 5 min. The phases were separated and the aqueous layer was extracted with EtOAc (3×10 mL). The combined organic layers were dried over MgSO$_4$, filtered and concentrated. Flash chromatography on silica (10% EtOAc in hexanes) afforded the title compound (17 mg, 0.038 mmol, 95%). HRMS (ESI+) 447.1771 (M+H$^+$).

f) 2-((5-(tert-Butyl)-7-(3,3-difluoropyrrolidin-1-yl)-3H-[1,2,3]triazolo[4,5-b]pyridin-3-yl)methyl)benzenethiol

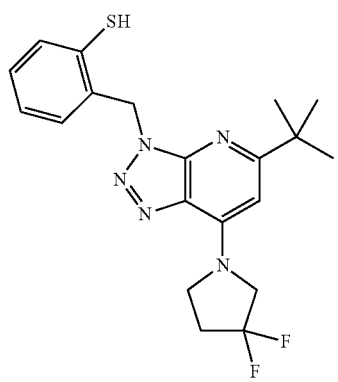 [SMILES: CC(C)(C)c1cc(N2CCC(F)(F)C2)c2nnn(Cc3ccccc3S)c2n1]

In analogy to the procedure described for the synthesis of 2-(2-((5-(tert-butyl)-7-(3,3-difluoropyrrolidin-1-yl)-3H-[1,2,3]triazolo[4,5-d]pyrimidin-3-yl)methyl)phenyl)ethanethiol (example 29, step d) the title compound was prepared from S-(2-((5-(tert-butyl)-7-(3,3-difluoropyrrolidin-1-yl)-3H-[1,2,3]triazolo[4,5-b]pyridin-3-yl)methyl)phenyl)ethanethioate (61 mg, 0.14 mmol, 1.0 equiv) and isolated as crude material (53 mg) to be used in the subsequent step without purification.

g) 2-[[2-[[5-tert-Butyl-7-(3,3-difluoropyrrolidin-1-yl)triazolo[4,5-d]pyrimidin-3-yl]methyl]phenyl]disulfanyl]ethanol In analogy to the procedure described for the synthesis of 2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanol (example 28) the title compound was prepared from crude 2-((5-(tert-butyl)-7-(3,3-difluoropyrrolidin-1-yl)-3H-[1,2,3]triazolo[4,5-b]pyridin-3-yl)methyl)benzenethiol (20 mg, 0.049 mmol, 1.0 equiv) and mercaptoethanol and isolated by preparative TLC (10% EtOAc in CH$_2$Cl$_2$) (11 mg, 0.023 mmol, 46%). HRMS (ESI+) 481.1645 (M+H$^+$).

Example 37

5-tert-butyl-7-(3,3-Difluoropyrrolidin-1-yl)-3-[[2-(pyridin-2-yldisulfanyl)phenyl]methyl]triazolo[4,5-d]pyrimidine In analogy to the procedure described for the synthesis of 2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanol (example 28) the title compound was prepared from crude 2-((5-(tert-butyl)-7-(3,3-difluoropyrro- lidin-1-yl)-3H-[1,2,3]triazolo[4,5-b]pyridin-3-yl)methyl)benzenethiol (30 mg, 0.063 mmol, 1.0 equiv) and 2-mercaptopyridine and isolated by preparative TLC (20% EtOAc in hexanes) (20 mg, 0.034 mmol, 46%). HRMS (ESI+) 584.1312 (M+H$^+$).

Example 38

2-[[5-tert-Butyl-7-(3,3-difluoropyrrolidin-1-yl)triazolo[4,5-d]pyrimidin-3-yl]methyl]-3-ethynylbenzenesulfonyl fluoride

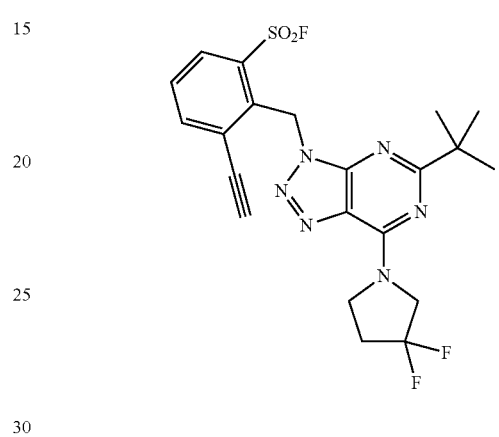

a) 3-Bromo-2-methylbenzene-1-sulfonyl fluoride

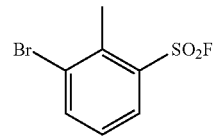

3-Bromo-2-methyl-benzene sulfonyl chloride (CAS 886501-61-7, 727 mg, 2.70 mmol. 1.00 equiv) was dissolved in acetone (8.5 mL) and water (0.5 mL). Potassium fluoride (783 mg, 13.5 mmol, 5.00 equiv) was added and the mixture was stirred overnight at rt. Most of the acetone was removed in a stream of nitrogen. The residue was partitioned between EtOAc (100 mL) and water (20 mL). The aqueous phase was discarded. The organic phase was washed with brine (20 mL), dried over MgSO$_4$, filtered and concentrated to yield a colorless solid (628 mg, 2.48 mmol, 92%). HRMS (MALDI+) 251.9250 (M$^+$).

b) 2-Methyl-3-((trimethylsilyl)ethynyl)benzene-1-sulfonyl fluoride

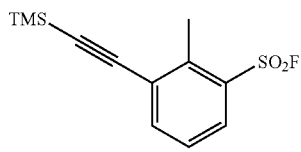 [SMILES: Cc1c(C#C[Si](C)(C)C)cccc1S(=O)(=O)F]

3-Bromo-2-methylbenzene-1-sulfonyl fluoride (628 mg, 2.48 mmol, 1.00 equiv), Pd(PPh$_3$)Cl$_2$ (174 mg, 0.25 mmol, 0.10 equiv) and CuI (71 mg, 0.37 mmol, 0.15 equiv) were place in a 25 mL pear-shaped flask. After evacuation and backfilling with nitrogen (2×), MeCN (12.4 mL) was added, followed by DIPEA (867 µt, 4.96 mmol, 2.00 equiv). Nitrogen was bubbled through the black solution for 5 minutes, before TMS-acetylene (696 µL, 4.96 mmol, 2.00 equiv) was added. The flask was capped and placed in a preheated oilbath (50° C.). After 3 h, additional TMS-acetylene (2.00 equiv) was added and stirring was continued at 50° C. overnight. After 24 h, the mixture was cooled to rt, filtered over celite and partitioned between water and EtOAc. The aqueous phase was extracted with EtOAc (3×20 mL). The combined organics were washed with water and brine, dried over MgSO$_4$, filtered and concentrated. Flash chromatography on silica (0.7% EtOAc in hexanes) afforded a brown oil that solidified upon standing (purity 94%, 610 mg, 2.12 mmol, 85%). NMR analysis indicates ca. 6% residual starting material. HRMS (MALDI+) 270.0541 (M+).

c) 2-(Bromomethyl)-3-((trimethylsilyl)ethynyl)benzene-1-sulfonyl fluoride

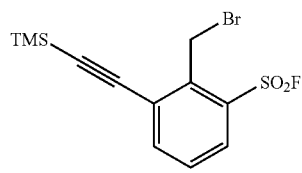 [SMILES: C[Si](C)(C)C#Cc1cccc(S(=O)(=O)F)c1CBr]

2-Methyl-3-((trimethyl silyl)ethynyl)benzene-1-sulfonyl fluoride (26 mg, 0.096 mmol, 1.00 equiv) was combined with NBS (86 mg, 0.48 mmol, 5.00 equiv), AIBN (2 mg, 0.012 mmol, 0.13 equiv) and MeCN (0.5 mL). The mixture was stirred overnight at 80° C. The volatiles were removed and the residue purified by preparative TLC to yield the title compound as colorless oil (15 mg, 0.043 mmol, 48%). HRMS (MALDI+) 370.9543 (M+Na+). (Note: the reaction never went to completion, also not if more NBS/AIBN is added).

d) 2-[[5-tert-Butyl-7-(3,3-difluoropyrrolidin-1-yl) triazolo[4,5-d]pyrimidin-3-yl]methyl]-3-ethynylbenzenesulfonyl fluoride 2-(Bromomethyl)-3-((trimethylsilyl)ethynyl)benzene-1-sulfonyl fluoride (30 mg, 0.086 mmol, 1.00 equiv) was combined with DMF (0.4 mL), trimethylamine (18 µL, 0.13 mmol, 1.5 equiv) and 5-tert-butyl-7-(3,3-difluoro-pyrrolidin-1-yl)-3H-[1,2,3]triazolo[4,5-d]pyrimidine (CAS 1438465-59-8, 27 mg, 0.095 mmol, 1.1 equiv). After 30 min, the mixture was diluted with EtOAc (100 mL), washed with 5% aq. LiCl (2×20 mL) and brine (20 mL), dried over MgSO$_4$, filtered and concentrated. Flash chromatography on silica (5% EtOAc in hexanes) afforded a mixture of two regioisomeric alkylation products (14 mg). The mixture was dissolved in THF (0.5 mL) and trimethylamine trihydrofluoride (8.2 mg in 0.1 mL THF, 0.051 mmol, 2.0 equiv) was added. After 4 h, the mixture was diluted with EtOAc (15 mL), washed with sat. aq. sodium bicarbonate and brine (3 mL each). Drying over MgSO$_4$, filtration and concentration afforded crude material, which was purified by pTLC (25% EtOAc in hexanes) to give the title compound as colorless oil (5 mg, 0.011 mmol, 13% over 2 steps). HRMS (ESI+) 479.1474 (M+H+).

Example 39

Pharmacological Tests

The following tests were carried out in order to determine the activity of the compounds of formula (I):

Radioligand Binding Assay

The affinity of the compounds of the invention for cannabinoid receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl$_2$, 2.5 mM EDTA, and 0.5% (wt/vol) fatty acid free BSA, pH 7.4 for CB1 receptor and 50 mM Tris, 5 mM MgCl$_2$, 2.5 mM EGTA, and 0.1% (wt/vol) fatty acid free BSA, pH 7.4 for CB2 receptor) in a total volume of 0.2 mL for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using non-linear regression analysis (Activity Base, ID Business Solution, Limited), with the Kd values for [$^3$H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

The compounds according to formula (I) have an activity in the above assay (Ki) particularly of 0.5 nM to 10 µM, more particularly of 0.5 nM to 3 µM and most particularly of 0.5 nM to 100 nM.

All compounds are CB2 binders with Ki values below 3 uM and selectivity versus CB1 in the corresponding assay of at least 3 fold.

| Example | human CB2 Ki [µM] | human CB1 Ki [µM] |
|---|---|---|
| 1 | 0.016 | >10.000 |
| 2 | 0.011 | 1.956 |
| 3 | 0.283 | >10.000 |
| 4 | 0.088 | 3.832 |
| 5 | 0.091 | >10.000 |
| 6 | 0.300 | 5.361 |
| 7 | 0.006 | 0.931 |
| 8 | 0.085 | 1.471 |
| 9 | 0.383 | >10.000 |
| 10 | 0.153 | >10.000 |
| 11 | 0.640 | 8.000 |
| 12 | 2.497 | 2.808 |
| 13 | 1.564 | >10.000 |
| 14 | 0.137 | >10.000 |
| 15 | 1.360 | 5.637 |
| 16 | 0.426 | >10.000 |
| 17 | 0.210 | 2.289 |
| 18 | 1.029 | >10.000 |
| 19 | 1.372 | >10.000 |
| 20 | 1.304 | >10.000 |
| 21 | 0.729 | 2.453 |
| 22 | 1.239 | 6.435 |
| 23 | 1.460 | 1.454 |
| 24 | 1.127 | 3.289 |
| 25 | 0.009 | 0.211 |
| 26 | 0.630 | >10.000 |
| 27 | 0.262 | 3.039 |
| 28 | 0.138 | 1.076 |
| 29 | 0.006 | 0.205 |
| 30 | 0.246 | >10.000 |
| 31 | 0.027 | 1.357 |
| 32 | 0.072 | 1.864 |
| 33 | 0.063 | 0.588 |
| 34 | 0.177 | 0.230 |

| Example | human CB2 Ki [µM] | human CB1 Ki [µM] |
|---|---|---|
| 35 | 0.005 | 0.135 |
| 36 | 0.095 | 0.560 |
| 37 | 0.541 | 2.577 |
| 38 | 0.001 | 0.311 | cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µL and incubated for 30 min at 30° C. Using the cAMP-Nano-TRF detection kit the assay (Roche Diagnostics) was stopped by the addition of 50 µL lysis reagent (Tris, NaCl, 1.5% Triton X100, 2.5% NP40, 10% $NaN_3$) and 50 µL detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

β-Arrestin Translocation Assay-PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 20 µL cell plating reagent 2 (Discoverx #93-0563R2A). After incubation at 37° C. (5% $CO_2$, 95% relative humidity) overnight, 5 µL of test compound was added (1% final DMSO concentration) and the incubation continued at 30° C. for 90 min. Detection reagent (12 µL) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

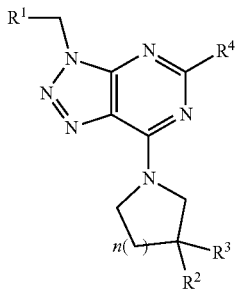

wherein

R¹ is a ring selected from phenyl and [1,2,5]oxadiazolyl wherein said ring is substituted with one substituent selected from halosulfonyl, halosulfonylalkyl, isothiocyanatoalkyl, isothiocyanato, aminoalkyldisulfanylalkyl, hydroxyalkyldisulfanylalkyl, hydroxyalkyldisulfanyl, aminoalkyldisulfanyl, halogen, alkyl, pyridinyldisulfanylalkyl, benzotriazolylsulfonylalkyl, dihydroxyalkyldisulfanylalkyl and pyridinyldisulfanyl and optionaly further substituted with cyano;

R² and R³ are independently selected from hydrogen, hydroxyl, halogen, thiohydroxyl, thiohydroxyazetidinyl, azido, isothiocyanato and alkyl disulfanyl;

provided that at least one of R¹, R² and R³ is a group comprising sulfonyl, isothiocyanato, disulfanyl, thiohydroxyl or azido;

R⁴ is alkyl or phenylhaloalkyl; and n is 0 or 1;

or a pharmaceutically acceptable salt or ester thereof.

2. The compound according to claim 1, wherein R¹ is a ring selected from phenyl and [1,2,5]oxadiazolyl wherein said ring is substituted with one substituent selected from halosulfonyl, halosulfonylalkyl, isothiocyanatoalkyl, isothiocyanato, halogen, alkyl, hydroxyalkyldisulfanylalkyl, pyridinyldisulfanylalkyl, dihydroxyalkyldisulfanylalkyl and optionaly further substituted with cyano.

3. The compound according to claim 1, wherein R¹ is a ring selected from phenyl and [1,2,5]oxadiazolyl wherein said ring is substituted with one substituent selected from fluorosulfonyl, fluorosulfonylmethyl, isothiocyanatomethyl, isothiocyanato, chloro, methyl, hydroxyethyldisulfanylethyl, fluorosulfonylethyl, pyridinyldisulfanylethyl, dihydroxyethyldisulfanylethyl and optionaly further substituted with cyano.

4. The compound according to claim 1, wherein R¹ is fluorosulfonylphenyl, fluorosulfonylmethylphenyl, isothiocyanatomethylphenyl, isothiocyanatophenyl, chlorophenyl, methyl[1,2,5]oxadiazolyl, hydroxyethyldisulfanylethylphenyl, fluorosulfonylethylphenyl, pyridinyldisulfanylethylphenyl, dihydroxyethyldisulfanylethylphenyl or (fluorosulfonyl)(cyano)phenyl.

5. The compound according to claim 1, wherein R² is hydrogen and R³ is hydroxyl, thiohydroxyl, azido, isothiocyanato or methyldisulfanyl, or R² and R³ are both fluoro.

6. The compound according to claim 1, wherein R⁴ is tert-butyl or phenyldifluoromethyl.

7. The compound according to claim 1, wherein n is 1.

8. The compound according to claim 1 selected from the group consisting of:

2-({5-tert-butyl-7-[(3S)-3-hydroxypyrrolidin-1-yl]-3H-[1,2,3]triazolo[4,5-d]pyrimidin-3-yl}methyl)benzene-1-sulfonyl fluoride;

(2-{[5-tert-butyl-7-(3,3-difluoropyrrolidin-1-yl)-3H-[1,2,3]triazolo[4,5-d]pyrimidin-3-yl]methyl}phenyl)methanesulfonyl fluoride;

[2-({5-tert-butyl-7-[(3S)-3-hydroxypyrrolidin-1-yl]-3H-[1,2,3]triazolo[4,5-d]pyrimidin-3-yl}methyl)phenyl]methanesulfonyl fluoride;

5-tert-butyl-7-(3,3-difluoropyrrolidin-1-yl)-3-{[2-(isothiocyanatomethyl)phenyl]methyl}-3H-[1,2,3]triazolo[4,5-d]pyrimidine;

(3S)-1-(5-tert-butyl-3-{[2-(isothiocyanatomethyl)phenyl]methyl}-3H-[1,2,3]triazolo[4,5-d]pyrimidin-7-yl)pyrrolidin-3-ol;

5-tert-butyl-7-(3,3-difluoropyrrolidin-1-yl)-3-[(2-isothiocyanatophenyl)methyl]-3H-[1,2,3]triazolo[4,5-d]pyrimidine;

2-{[5-tert-butyl-7-(3,3-difluoropyrrolidin-1-yl)-3H-[1,2,3]triazolo[4,5-d]pyrimidin-3-yl]methyl}benzene-1-sulfonyl fluoride;

2-{[(2-{[5-tert-butyl-7-(3,3-difluoropyrrolidin-1-yl)-3H-[1,2,3]triazolo[4,5-d]pyrimidin-3-yl]methyl}phenyl)methyl]disulfanyl}ethan-1-amine;

2-{[(2-{[5-tert-butyl-7-(3,3-difluoropyrrolidin-1-yl)-3H-[1,2,3]triazolo[4,5-d]pyrimidin-3-yl]methyl}phenyl)methyl]disulfanyl}ethan-1-ol;

2-[(2-{[5-tert-butyl-7-(3,3-difluoropyrrolidin-1-yl)-3H-[1,2,3]triazolo[4,5-d]pyrimidin-3-yl]methyl}phenyl)disulfanyl]ethan-1-ol;

2-[(2-{[5-tert-butyl-7-(3,3-difluoropyrrolidin-1-yl)-3H-[1,2,3]triazolo[4,5-d]pyrimidin-3-yl]methyl}phenyl)disulfanyl]ethan-1-amine;

2-{[2-({5-[difluoro(phenyl)methyl]-7-(3,3-difluoropyrrolidin-1-yl)-3H-[1,2,3]triazolo[4,5-d]pyrimidin-3-yl}methyl)phenyl]disulfanyl}ethan-1-amine;

2-({[2-({5-[difluoro(phenyl)methyl]-7-(3,3-difluoropyrrolidin-1-yl)-3H-[1,2,3]triazolo[4,5-d]pyrimidin-3-yl}methyl)phenyl]methyl}disulfanyl)ethan-1-amine;

2-({5-[difluoro(phenyl)methyl]-7-[(3S)-3-hydroxypyrrolidin-1-yl]-3H-[1,2,3]triazolo[4,5-d]pyrimidin-3-yl}methyl)benzene-1-sulfonyl fluoride;

2-({5-[difluoro(phenyl)methyl]-7-(3,3-difluoropyrrolidin-1-yl)-3H-[1,2,3]triazolo[4,5-d]pyrimidin-3-yl}methyl)benzene-1-sulfonyl fluoride;

[2-({5-[difluoro(phenyl)methyl]-7-[(3S)-3-hydroxypyrrolidin-1-yl]-3H-[1,2,3]triazolo[4,5-d]pyrimidin-3-yl}methyl)phenyl]methanesulfonyl fluoride;

[2-({5-[difluoro(phenyl)methyl]-7-(3,3-difluoropyrrolidin-1-yl)-3H-[1,2,3]triazolo[4,5-d]pyrimidin-3-yl}methyl)phenyl]methanesulfonyl fluoride;

(3S)-1-(5-[difluoro(phenyl)methyl]-3-{[2-(isothiocyanatomethyl)phenyl]methyl}-3H-[1,2,3]triazolo[4,5-d]pyrimidin-7-yl)pyrrolidin-3-ol;

5-[difluoro(phenyl)methyl]-7-(3,3-difluoropyrrolidin-1-yl)-3-{[2-(isothiocyanatomethyl)phenyl]methyl}-3H-[1,2,3]triazolo[4,5-d]pyrimidine;

5-[difluoro(phenyl)methyl]-7-(3,3-difluoropyrrolidin-1-yl)-3-[(2-isothiocyanatophenyl)methyl]-3H-[1,2,3]triazolo[4,5-d]pyrimidine;

1-{5-tert-butyl-3-[(2-chlorophenyl)methyl]-3H-[1,2,3]triazolo[4,5-d]pyrimidin-7-yl}pyrrolidine-3-thiol;

1-{5-tert-butyl-3-[(2-chlorophenyl)methyl]-3H-[1,2,3]triazolo[4,5-d]pyrimidin-7-yl}azetidine-3-thiol;

(3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

(3R)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

(3S)-1-{5-tert-butyl-3-[(2-chlorophenyl)methyl]-3H-[1,2,3]triazolo[4,5-d]pyrimidin-7-yl}pyrrolidine-3-thiol;

(3R)-1-{5-tert-butyl-3-[(2-chlorophenyl)methyl]-3H-[1,2,3]triazolo[4,5-d]pyrimidin-7-yl}pyrrolidine-3-thiol 7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine;

5-tert-butyl-3-[(2-chlorophenyl)methyl]-7-(3-isothiocyanatopyrrolidin-1-yl)-3H-[1,2,3]triazolo[4,5-d]pyrimidine;

5-tert-butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine;

7-(3-azidopyrrolidin-1-yl)-5-tert-butyl-3-[(2-chlorophenyl)methyl]-3H-[1,2,3]triazolo[4,5-d]pyrimidine;

5-[difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine;

3-[(2-chlorophenyl)methyl]-5-[difluoro(phenyl)methyl]-7-[3-(methyldisulfanyl)pyrrolidin-1-yl]-3H-[1,2,3]triazolo[4,5-d]pyrimidine;

7-(3-azidopyrrolidin-1-yl)-5-[difluoro(phenyl)methyl]-3-[(4-methyl-1,2,5-oxadiazol-3-yl)methyl]-3H-[1,2,3]triazolo[4,5-d]pyrimidine;

7-(3-azidopyrrolidin-1-yl)-3-[(2-chlorophenyl)methyl]-5-[difluoro(phenyl)methyl]-3H-[1,2,3]triazolo[4,5-d]pyrimidine;

3-[(2-chlorophenyl)methyl]-5-[difluoro(phenyl)methyl]-7-(3-isothiocyanatopyrrolidin-1-yl)-3H-[1,2,3]triazolo[4,5-d]pyrimidine;

5-[difluoro(phenyl)methyl]-7-(3-isothiocyanatopyrrolidin-1-yl)-3-[(4-methyl-1,2,5-oxadiazol-3-yl)methyl]-3H-[1,2,3]triazolo[4,5-d]pyrimidine;

2-[[5-[difluoro(phenyl)methyl]-7-[(3S)-3-hydroxypyrrolidin-1-yl]triazolo[4,5-d]pyrimidin-3-yl]methyl]benzenesulfonyl fluoride;

2-[[2-[[5-tert-butyl-7-(3,3-difluoropyrrolidin-1-yl)triazolo[4,5-d]pyrimidin-3-yl]methyl]phenyl]methyldisulfanyl]ethanol;

2-[[5-[difluoro(phenyl)methyl]-7-(3,3-difluoropyrrolidin-1-yl)triazolo[4,5-d]pyrimidin-3-yl]methyl]benzenesulfonyl fluoride;

5-[difluoro(phenyl)methyl]-7-(3,3-difluoropyrrolidin-1-yl)-3-[[2-[2-(pyridin-2-yldisulfanyl)ethyl]phenyl]methyl]triazolo[4,5-d]pyrimidine;

2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanol;

2-[2-[2-[[5-tert-butyl-7-(3,3-difluoropyrrolidin-1-yl)triazolo[4,5-d]pyrimidin-3-yl]methyl]phenyl]ethyldisulfanyl]ethanol;

3-[[2-[2-(benzotriazol-1-ylsulfonyl)ethyl]phenyl]methyl]-5-tert-butyl-7-(3,3-difluoropyrrolidin-1-yl)triazolo[4,5-d]pyrimidine;

2-[2-[[5-tert-butyl-7-(3,3-difluoropyrrolidin-1-yl)triazolo[4,5-d]pyrimidin-3-yl]methyl]phenyl]ethanesulfonyl fluoride;

5-tert-butyl-7-(3,3-difluoropyrrolidin-1-yl)-3-[[2-[2-(pyridin-2-yldisulfanyl)ethyl]phenyl]methyl]triazolo[4,5-d]pyrimidine;

2-[2-[[5-tert-butyl-7-(3,3-difluoropyrrolidin-1-yl)triazolo[4,5-d]pyrimidin-3-yl]methyl]phenyl]ethyldisulfanyl]ethanamine;

2-[2-[2-[[5-[difluoro(phenyl)methyl]-7-(3,3-difluoropyrrolidin-1-yl)triazolo[4,5-d]pyrimidin-3-yl]methyl]phenyl]ethyldisulfanyl]ethanamine;

3-[2-[2-[[5-tert-butyl-7-(3,3-difluoropyrrolidin-1-yl)triazolo[4,5-d]pyrimidin-3-yl]methyl]phenyl]ethyldisulfanyl]propane-1,2-diol;

2-[[2-[[5-tert-butyl-7-(3,3-difluoropyrrolidin-1-yl)triazolo[4,5-d]pyrimidin-3-yl]methyl]phenyl]disulfanyl]ethanol;

5-tert-butyl-7-(3,3-difluoropyrrolidin-1-yl)-3-[[2-(pyridin-2-yldisulfanyl)phenyl]methyl]triazolo[4,5-d]pyrimidine; and 2-[[5-tert-butyl-7-(3,3-difluoropyrrolidin-1-yl)triazolo[4,5-d]pyrimidin-3-yl]methyl]-3-ethynylbenzenesulfonyl fluoride;

or a pharmaceutically acceptable salt thereof.

9. The compound according to claim 1 selected from the group consisting of:

2-({5-tert-butyl-7-[(3S)-3-hydroxypyrrolidin-1-yl]-3H-[1,2,3]triazolo[4,5-d]pyrimidin-3-yl}methyl)benzene-1-sulfonyl fluoride;

(2-{[5-tert-butyl-7-(3,3-difluoropyrrolidin-1-yl)-3H-[1,2,3]triazolo[4,5-d]pyrimidin-3-yl]methyl}phenyl)methanesulfonyl fluoride;

5-tert-butyl-7-(3,3-difluoropyrrolidin-1-yl)-3-[2-(isothiocyanatomethyl)phenyl]methyl 1-3H-[1,2,3]triazolo[4,5-d]pyrimidine;

(3S)-1-(5-tert-butyl-3-1 [2-(isothiocyanatomethyl)phenyl]methyl-3H-[1,2,3]triazolo[4,5-d]pyrimidin-7-yl)pyrrolidin-3-ol;

5-tert-butyl-7-(3,3-difluoropyrrolidin-1-yl)-3-[(2-isothiocyanatophenyl)methyl]-3H-[1,2,3]triazolo[4,5-d]pyrimidine;

2-{[5-tert-butyl-7-(3,3-difluoropyrrolidin-1-yl)-3H-[1,2,3]triazolo[4,5-d]pyrimidin-3-yl]methyl}benzene-1-sulfonyl fluoride;

1-{5-tert-butyl-3-[(2-chlorophenyl)methyl]-3H-[1,2,3]triazolo[4,5-d]pyrimidin-7-yl}pyrrolidine-3-thiol;

(3S)-1-{5-tert-butyl-3-[(4-methyl-1,2,5-oxadiazol-3-yl)methyl]-3H-[1,2,3]triazolo[4,5-d]pyrimidin-7-yl}pyrrolidine-3-thiol;

7-(3-azidopyrrolidin-1-yl)-5-tert-butyl-3-[(4-methyl-1,2,5-oxadiazol-3-yl)methyl]-3H-[1,2,3]triazolo[4,5-d]pyrimidine;

5-tert-butyl-7-(3-isothiocyanatopyrrolidin-1-yl)-3-[(4-methyl-1,2,5-oxadiazol-3-yl)methyl]-3H-[1,2,3]triazolo[4,5-d]pyrimidine;

5-[difluoro(phenyl)methyl]-7-[3-(methyldisulfanyl)pyrrolidin-1-yl]-3-[(4-methyl-1,2,5-oxadiazol-3-yl)methyl]-3H-[1,2,3]triazolo[4,5-d]pyrimidine;

7-(3-azidopyrrolidin-1-yl)-3-[(2-chlorophenyl)methyl]-5-[difluoro(phenyl)methyl]-3H-[1,2,3]triazolo[4,5-d]pyrimidine;

2-[[5-[difluoro(phenyl)methyl]-7-(3,3-difluoropyrrolidin-1-yl)triazolo[4,5-d]pyrimidin-3-yl]methyl]benzenesulfonyl fluoride;

2-[2-[2-[[5-tert-butyl-7-(3,3-difluoropyrrolidin-1-yl)triazolo[4,5-d]pyrimidin-3-yl]methyl]phenyl]ethyldisulfanyl]ethanol;

2-[2-[[5-tert-butyl-7-(3,3-difluoropyrrolidin-1-yl)triazolo[4,5-d]pyrimidin-3-yl]methyl]phenyl]ethanesulfonyl fluoride;

5-tert-butyl-7-(3,3-difluoropyrrolidin-1-yl)-3-[[2-[2-(pyridin-2-yldisulfanyl)ethyl]phenyl]methyl]triazolo[4,5-d]pyrimidine;

3-[2-[2-[[5-tert-butyl-7-(3,3-difluoropyrrolidin-1-yl)triazolo[4,5-d]pyrimidin-3-yl]methyl]phenyl]ethyldisulfanyl]propane-1,2-diol; and 2-[[5-tert-butyl-7-(3,3-difluoropyrrolidin-1-yl)triazolo[4,5-d]pyrimidin-3-yl]methyl]-3-ethynylbenzenesulfonyl fluoride;

or a pharmaceutically acceptable salt thereof.

10. A process for the manufacture of a compound according to claim 1 comprising the reaction of a compound of formula (A)

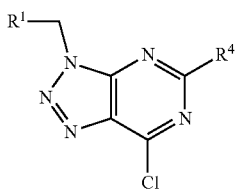

in the presence of a compound of formula (B)

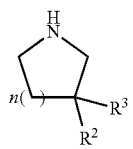

and a base, wherein $R^1$ to $R^4$ and n are as defined in claim 1.

11. A compound manufactured according to a process of claim 10.

12. A pharmaceutical composition comprising a compound of claim 1, or a pharmaceutically acceptable salt or ester thereof, and a therapeutically inert carrier.

13. A method for the treatment of pain, which method comprises administering an effective amount of a compound of claim 1, or a pharmaceutically acceptable salt or ester thereof, to a patient in need thereof.

14. The compound according to claim 4, wherein $R^2$ is hydrogen and $R^3$ is hydroxyl, thiohydroxyl, azido, isothiocyanato or methyldisulfanyl, or $R^2$ and $R^3$ are both fluoro.

15. The compound according to claim 14, wherein $R^4$ is tert-butyl or phenyldifluoromethyl.

16. The compound according to claim 15, wherein n is 1.

17. The method of claim 13, wherein the pain is a neuropathic pain.

* * * * *